US010793622B2

(12) United States Patent
Duthe et al.

(10) Patent No.: US 10,793,622 B2
(45) Date of Patent: Oct. 6, 2020

(54) CONTINUOUS MULTISTEP PROCESS FOR PURIFYING ANTIBODIES

(71) Applicant: SANOFI, Paris (FR)

(72) Inventors: Didier Duthe, Paris (FR); Celine Hemet, Paris (FR); Laure Landric-Burtin, Paris (FR); Benoit Mothes, Paris (FR)

(73) Assignee: SANOFI, Paris (FR)

( * ) Notice: Subject to any disclaimer, the term of this patent is extended or adjusted under 35 U.S.C. 154(b) by 506 days.

(21) Appl. No.: 14/889,397

(22) PCT Filed: May 6, 2014

(86) PCT No.: PCT/EP2014/059246
§ 371 (c)(1),
(2) Date: Nov. 5, 2015

(87) PCT Pub. No.: WO2014/180852
PCT Pub. Date: Nov. 13, 2014

(65) Prior Publication Data
US 2016/0083454 A1 Mar. 24, 2016

(30) Foreign Application Priority Data
May 6, 2013 (EP) ..................................... 13305593

(51) Int. Cl.
*C07K 1/16* (2006.01)
*C07K 1/36* (2006.01)
*C07K 16/06* (2006.01)
*C12M 1/00* (2006.01)
*C07K 16/40* (2006.01)

(52) U.S. Cl.
CPC .............. *C07K 16/065* (2013.01); *C07K 1/16* (2013.01); *C07K 1/36* (2013.01); *C07K 16/40* (2013.01); *C12M 47/12* (2013.01)

(58) Field of Classification Search
None
See application file for complete search history.

(56) References Cited

U.S. PATENT DOCUMENTS

| | | | |
|---|---|---|---|
| 5,891,741 | A | 4/1999 | Siiman et al. |
| 6,602,855 | B2 | 8/2003 | Jackowski et al. |
| 2002/0009445 | A1 | 1/2002 | Du et al. |
| 2007/0259453 | A1 | 11/2007 | Engstrand et al. |
| 2009/0304710 | A1* | 12/2009 | Park .................. A61K 47/6867 424/158.1 |
| 2011/0065901 | A1* | 3/2011 | Soice .................... C07K 16/00 530/388.1 |
| 2011/0073548 | A1* | 3/2011 | Williams ............... G01N 30/28 210/739 |
| 2011/0237781 | A1* | 9/2011 | Lebing ............... C07K 14/8125 530/395 |
| 2012/0065380 | A1* | 3/2012 | Yoo .................... C07K 16/2863 530/387.3 |
| 2012/0238730 | A1* | 9/2012 | Dong ............... A61K 39/39591 530/389.1 |
| 2012/0322099 | A1 | 12/2012 | Lapen et al. |
| 2013/0295082 | A1* | 11/2013 | Garidel .................. C07K 16/18 424/133.1 |
| 2014/0323698 | A1 | 10/2014 | Duthe et al. |

FOREIGN PATENT DOCUMENTS

| | | |
|---|---|---|
| CN | 1266907 A | 9/2000 |
| CN | 1504482 A | 6/2004 |
| CN | 1814775 A | 8/2006 |
| CN | 101730707 B | 12/2014 |
| EP | 2 360 183 A1 | 8/2011 |
| EP | 2 415 779 A1 | 2/2012 |
| JP | 2008-501317 A | 1/2008 |
| JP | 2008-533977 A | 8/2008 |
| RU | 2145873 C1 | 2/2000 |
| TW | 201313735 A | 4/2013 |
| WO | 1989/003840 A1 | 5/1989 |
| WO | 1995/008574 A1 | 3/1995 |
| WO | 2005/103084 A2 | 11/2005 |
| WO | 2006/043895 A1 | 4/2006 |
| WO | 2006/099875 A1 | 9/2006 |
| WO | 2009/007451 A1 | 1/2009 |
| WO | 2009/099829 A1 | 8/2009 |
| WO | 2009/111347 A1 | 9/2009 |
| WO | WO 2009/138484 A2 | 11/2009 |
| WO | 2010/071208 A1 | 6/2010 |
| WO | 2010/082894 A1 | 7/2010 |
| WO | 2011/049798 A1 | 4/2011 |
| WO | 2011/090719 A2 | 7/2011 |
| WO | 2011/090719 A3 | 7/2011 |

(Continued)

OTHER PUBLICATIONS

Uwe Gottschalk "Bioseparation in Antibody manufacturing: the good, the bad and the ugly" Biotechnol. Prog, 24, 496-503 (Year: 2008).*
Christiana Boi "membrane adsorbers as purificaiton tools for monoclonal antibody purificaiton" J. Chromatography B, 848 19-27 (Year: 2007).*
Eriksson et al. (Feb. 2009) "MAb Contaminant Removal with a Multimodal Anion Exchanger," BioProcess International. 7:52-56.
GE Healthcare (Oct. 2009) "Rapid Process Development for Purification of a MAb Using AKTA(TM) Avant 25," Application Note 28-9573-47 AB. Accessible on the Internet at URL: https://www.gelifesciences.com/gehcls_images/GELS/Related%20Content/Files/1314787424814/litdoc28957347AB_20110831143417.pdf. [Last Accessed Jun. 9, 2016].

(Continued)

*Primary Examiner* — Daniel E Kolker
*Assistant Examiner* — James L Rogers
(74) *Attorney, Agent, or Firm* — Lathrop GPM LLP; James H. Velema; Judith L. Stone-Hulslander

(57) ABSTRACT

The invention provides a three-step chromatography process for small and large-scale purification of proteins, specifically monoclonal antibodies, using only four buffer solutions made from a mother solution.

23 Claims, 12 Drawing Sheets

(56) References Cited

FOREIGN PATENT DOCUMENTS

| WO | 2012135415 A1 | 10/2012 | |
| WO | WO-2012135415 A1 * | 10/2012 | ............... C07K 1/22 |
| WO | 2013/028330 A2 | 2/2013 | |
| WO | 2013/075849 A1 | 5/2013 | |
| WO | 2013075740 A1 | 5/2013 | |
| WO | WO-2013075740 A1 * | 5/2013 | ............. C07K 1/165 |

OTHER PUBLICATIONS

Horio et al: Eds. (2000) "12.2 Good's buffer," Basic Experimental Methods for Proteins and Enzymes (in Japanese). Revised 2nd Version. pp. 554-555. (a Japanese experimental protocol book in which Table 12-2 "Good's buffers" shows Bis-Tris at the second line, the relevant portion of this document).

Liu et al. (2010) "Recovery and purification process development for monoclonal antibody production," mAbs 2(5):480-499.

Qian et al. (2007) "Conjugating recombinant proteins to Pseudomonas aeruginosa ExoProtein A: A strategy for enhancing immunogenicity of malaria vaccine candidates," Vaccine. 25(20):3923-3933.

Riordan et al. (2009) "Design of salt-tolerant membrane adsorbers for viral clearance," Biotechnol. Bioeng. 103:920-929.

Verdoliva et al. (2002) "Affinity purification of polyclonal antibodies using a new all-D synthetic peptide ligand: comparison with protein A and protein G," J. Immunol. Methods. 271(1-2):77-88.

Zhou et al. (1993) "Purification and Characterization of the Prohormone Convertase PC1(PC3)*," J. Biol. Chem. 268(8):5615-5623.

International Search Report with Written Opinion corresponding to International Patent Application No. PCT/EP2012/059528, dated Jul. 26, 2012.

Written Opinion corresponding to International Patent Application No. PCT/EP2014/059246, dated Jul. 17, 2014.

Bruel et al. (2000) "Rhodopsin kinase: Expression in mammalian cells and a two-step purification," Proc. Natl. Acad. Sci. USA. 90(7):3010-3015.

GE Healthcare—Life Sciences (Nov. 2013) "Multimodal Chromatography Handbook," Document No. 29-0548-08 AA. Accessible on the Internet at URL: http://proteins.gelifesciences.com/~/media/protein-purification-ib/documents/handbooks/multimodal_chromatography.pdf?la=en. pp. 1-112. [Last Accessed on Jan. 4 2017].

Follman et al. (2004) "Factorial screening of antibody purification processes using three chromatography steps without protein A," J. Chromatogr. A. 1024:79-85.

Pollock et al. (Jan. 25, 2013) "Optimising the design and operation of semi-continuous affinity chromatography for clinical and commercial manufacture," J. Chromatogr. A. 1284:17-27.

U.S. Appl. No. 14/360,103 / 2014/0323698, filed May 22, 2014 / Oct. 30, 2014, Didier Duthe.

Boi, C. (2007) "Membrane adsorbers as purificaiton tools for monoclonal antibody purification," J. Chromatography B, vol. 848, pp. 19-27.

Gottschalk, U. (2008) "Bioseparation in Antibody Manufacturing: the Good, the Bad and the Ugly" Biotechnol. Prog., vol. 24, pp. 496-503.

Mahajan et al., "Improving affinity chromatography resin efficiency using semi-continuous chromatography" Journal of Chromatography A (2012), vol. 1227, pp. 154-162.

Shamashkin et al., "A tandem laboratory scale protein purification process using protein A affinity and anion exchange chromatograph operated in a weak partitioning mode" Biotechnology and Bioengineering (2013), vol. 110 (10), pp. 2655-2663.

The International Search Report (ISR) for PCT/EP2014/059246 dated Jul. 17, 2014, pp. 1-4.

Japan Biochemical Society: Eds. (1990) Protein I: Isolation, Purification and Properties. 1st Ed. pp. 324-327; provided with an English machine translation.

Landric-Burtin et al. (2011) "How to shorten downstream processing for Monoclonal antibodies," Presentation by Sanofi-Aventis, Biologics Center. European Downstream Technology Forum, May 24-25, 2011, Goettingen, Germany. 24 pages.

European Search Report in related European Patent Application No. EP 17 20 0909, dated Nov. 29, 2017 (5 pages).

\* cited by examiner

US 10,793,622 B2

CONTINUOUS MULTISTEP PROCESS FOR PURIFYING ANTIBODIES

This application is a national stage application under 35 U.S.C. § 371 of International Application No. PCT/EP2014/059246, filed May 6, 2014, which claims the benefit of European Patent Application No. EP 13305593.9, filed May 6, 2013, the disclosures of each of which are explicitly incorporated by reference herein.

TECHNICAL FIELD

The invention relates to a three-step chromatography process for small and large-scale purification of proteins, specifically monoclonal antibodies, using four buffer solutions.

BACKGROUND

Antibody purification can be one of the most costly aspects of bioproduction. Monoclonal antibodies (mAbs) are generally purified using a three-step, three resin chromatography process, using a specific buffer system at each step. This conventional purification process encompasses a capture step, followed by an ionic exchange step, and concludes with a polishing step, and usually takes 3 to 5 working days (including storages and open phases). In such conventional processes, these three steps are carried out in a sequence of distinct unit operations, which cannot be operated in a continuous mode as adjustment of pH, molarity and protein concentration are necessary between each step. Such a conventional purification process is schematized on FIG. 5. Accordingly, conventional purification processes generally require numerous different buffers as well as numerous storage units between each discontinued step. These conventional purification processes are thus prone to contaminations, technical failures and human errors. Additionally, since an interruption is needed between each step for concentrating the eluate, adjusting pH and conductivity and storing the eluate before the next step, and since a step cannot start before completion of the previous one, such conventional purification processes are particularly long and expensive, as it can be seen on FIG. 7.

With increasing cell culture titers and larger cell culture volumes being used for production, downstream processing is viewed as an industry bottleneck. This is particularly relevant to monoclonal antibody production, where the focus has shifted away from batch volume, and towards downstream processing capacity. Furthermore, early pre-clinical and clinical phase studies require larger amounts of antibodies that can be produced more rapidly. Therefore, a need exists in the industry for a process, which can be carried out in a continuous mode, for antibody purification, and for both a reduction in the time taken for obtaining batches, in the risks of contaminations, technical failures and human errors and in the process scale-up requirements.

SUMMARY OF INVENTION

The inventors have found a new method for purifying antibodies, said method comprising a limited number of steps in a continuous mode, using reduced amounts of resins and buffers while still allowing obtaining high yields of purified antibodies with an excellent degree of purity. The purified proteins are thus suitable for medical applications. Accordingly, the method may be used to purify proteins for clinical trials and/or for marketing of a pharmaceutical composition comprising the protein. Additionally, this method does not need any inter-step adjustment and can thus be carried out in a closed system from the harvest of proteins to be purified to the final product.

Briefly, this method comprises only three chromatographic steps in a continuous mode: one affinity chromatography, one multi-modal resin or cation-exchange chromatography, and one anion-exchange chromatography (AEX). These three chromatographic steps can be implemented in any order. In addition, it has been found that all buffers used during these three chromatography steps can be prepared starting from the same mother solution. These buffers advantageously comprise Bis Tris, for example in combination with NaCl, acetic acid, water, and optionally $NH_4Cl$. As there is no need for any buffer exchange, the method is easy to carry out, and is highly suitable for automation and/or for running in continuous mode. More particularly, it is possible to only use 4 buffers for the entire process, ensuring compatibility between all steps and enabling supply chain manufacturing and quality control savings and reduced storage needs.

The method of the invention further allows reducing or abolishing open phases (i.e. steps where the purification system is opened to carry out a manual operation such as preparing the chromatographic column for a new buffer, diluting the sample, or adjusting its pH), thereby reducing the risk of contamination and giving the possibility to work in a less classified environment. Additionally, since each chromatographic step of the method of the invention can use re-usable resins or, surprisingly can re-use disposable membrane adsorbers, the sequence of the three chromatographic steps can be renewed until obtaining the desired quantity without human handling. In particular, all the chromatographic steps of the method of the invention can be implemented using resins which can be reused at least 100 times or using membrane adsorbers which can be reused at least 50 times. The inventors indeed demonstrated that it was possible to use the same disposable membrane adsorber through at least 50 runs without losing stability. The process cycle times are thus shortened, the process scale-up requirements are minimized, and it is possible to reduce operation and storage expenses since volumes of resins and buffers can be reduced and disposable membrane adsorbers do not need to be stored after a batch. Therefore, the method of the invention allows both rapid cost effective production of batches and reducing the occupation time of the purification systems, as it can be seen on FIGS. 10 and 12, compared to FIGS. 9 and 11. It is thus suitable for scale-up and purification of recombinant proteins from the bench to the industrial scale.

A specific protocol has been set up and implemented for four different antibodies. In this protocol, the crude protein eluent obtained at the end of the first chromatographic step is directly passed over the second chromatography matrix, in particular over the second chromatography column or membrane adsorber, i.e. without undergoing any treatment like pH adjustment, buffer exchange or dilution, and the protein eluate obtained at the end of the second chromatographic step is also directly passed over the third chromatography matrix, in particular over the third chromatography column or membrane adsorber, i.e. without undergoing any treatment like pH adjustment, buffer exchange or dilution. This method is schematized on FIG. 6. Additionally, in this protocol, the protein containing solution is loaded over the first chromatography matrix, in particular over the first chromatography column or membrane adsorber, in successive runs (see Example 6), the successive runs starting as soon as the prior run is eluted from the first chromatographic step, as it can be seen on FIG. 8. This protocol has the advantage of being extremely rapid (about 2 hours for a sequence), leads to an improved yield (more than 90%), an improved purity and enables reducing both buffers and resins volumes used when columns are used, and reducing both buffers and storage facilities used when membrane adsorbers are used. Moreover, this process has the advantage of being extremely flexible since the size of the columns used and/or the number of runs can be easily adapted to the amount of proteins to be purified. In addition, it can be completely automated, run in continuous mode, and it does not comprise any open phase. Moreover, it was successfully carried out for four different antibodies without needing optimization.

The invention thus provides a method for purifying a protein from solution comprising a first chromatography step comprising passing equilibration buffer over a first chromatography matrix, in particular over a first chromatography column or membrane adsorber, passing the solution over the first chromatography matrix, in particular over the first chromatography column or membrane adsorber, passing equilibration buffer over the first chromatography matrix, in particular over the first chromatography column or membrane adsorber, passing wash buffer over the first chromatography matrix, in particular over the first chromatography column or membrane adsorber, passing equilibration buffer over the first chromatography matrix, in particular over the first chromatography column or membrane adsorber, and eluting a crude protein eluent from the first chromatography matrix, in particular from the first chromatography column or membrane adsorber, using a first elution buffer; a second chromatography step comprising passing equilibration buffer over a second chromatography matrix, in particular over a second chromatography column or membrane adsorber, passing the crude protein eluent over the second chromatography matrix, in particular over the second chromatography column or membrane adsorber, optionally passing equilibration buffer over the second chromatography matrix, in particular over the second chromatography column or membrane adsorber, and eluting a protein eluate from the second chromatography matrix, in particular from the second chromatography column or membrane adsorber, using a second elution buffer; and a third chromatography step comprising passing equilibration buffer over a third chromatography matrix, in particular over a third chromatography column or membrane adsorber, passing the protein eluate through the third chromatography matrix, in particular through the third chromatography column or membrane adsorber, in the flow-through mode, optionally passing wash buffer over the third chromatography matrix, in particular over the third chromatography column or membrane adsorber, and recovering purified protein from the flow-through of the third chromatography matrix, in particular of the third chromatography column or membrane adsorber.

The invention also provides a method for purifying a protein from a solution comprising a first chromatography step comprising passing equilibration buffer over a first chromatography matrix, in particular over a first chromatography column or membrane adsorber, passing a part of the solution over the first chromatography matrix, in particular over the first chromatography column or membrane adsorber, passing equilibration buffer over the first chromatography matrix, in particular over the first chromatography column or membrane adsorber, passing wash buffer over the first chromatography matrix, in particular over the first chromatography column or membrane adsorber, passing equilibration buffer over the first chromatography matrix, in particular over the first chromatography column or membrane adsorber, eluting a crude protein eluent from the first chromatography matrix, in particular from the first chromatography column or membrane adsorber, using a first elution buffer, and optionally passing sanitation buffer over the first chromatography matrix, in particular over the first chromatography column or membrane adsorber; a second chromatography step comprising passing equilibration buffer over a second chromatography matrix, in particular over a second chromatography column or membrane adsorber, passing the crude protein eluent over the second chromatography matrix, in particular over the second chromatography column or membrane adsorber, optionally passing equilibration buffer over the second chromatography matrix, in particular over the second chromatography column or membrane adsorber, eluting a protein eluate from the second chromatography matrix, in particular from the second chromatography column or membrane adsorber, using a second elution buffer, and optionally passing sanitation buffer over the second chromatography matrix, in particular over the second chromatography column or membrane adsorber; a third chromatography step comprising passing equilibration buffer over a third chromatography matrix, in particular over a third chromatography column or membrane adsorber, passing the protein eluate through the third chromatography matrix, in particular through the third chromatography column or membrane adsorber, in the flow-through mode, optionally passing wash buffer over the third chromatography matrix, in particular over the third chromatography column or membrane adsorber, recovering purified protein from the flow-through of the third chromatography matrix, in particular of the third chromatography column or membrane adsorber, and optionally passing sanitation buffer over the third chromatography matrix, in particular over the third chromatography column or membrane adsorber; renewing successively the first, second and third chromatography steps with another part of the solution until all the solution is used, and collecting the purified proteins recovered at the end of each third chromatography step.

In one embodiment of the invention, each of the buffers comprises Bis Tris. In another embodiment, each buffer comprises Bis Tris, acetic acid, NaCl, water, and optionally $NH_4Cl$. The use of Bis Tris buffers in the method of the invention is particularly important because it enables avoiding adjusting pH between the three chromatographic steps and thus running the method in a closed system from the first to the last step.

In one embodiment, one of the chromatography matrices is a Protein A matrix. In one embodiment, one of the chromatography matrices is a multi-modal resin or cation-exchange chromatography matrix. In one embodiment, one of the chromatography matrices is an anion-exchange chromatography matrix.

In a particular embodiment, the method of the invention comprises a Protein A chromatography matrix, a multi-modal resin or cation-exchange chromatography matrix and an anion-exchange chromatography matrix, said matrices being used in any order in the three chromatographic steps.

In one embodiment of the invention, the first chromatography matrix is a Protein A matrix, the second chromatography matrix is a multi-modal resin or cation-exchange chromatography matrix and the third chromatography matrix is an anion-exchange chromatography matrix.

In one embodiment of the invention, each chromatography matrix is a chromatography column. In a particular embodiment of that embodiment, the first chromatography matrix is a Protein A column, the second chromatography matrix is a multi-modal resin chromatography column and the third chromatography matrix is an anion-exchange chromatography column.

In another embodiment of the invention, each chromatography matrix is a chromatography membrane adsorber. In a particular embodiment of that embodiment, the first chromatography matrix is a Protein A membrane adsorber, the second chromatography matrix is a cation-exchange membrane adsorber and the third chromatography matrix is an anion-exchange membrane adsorber.

In one embodiment of the invention, the protein being purified is an antibody. In another embodiment, the antibody is a monoclonal antibody.

In one embodiment of the invention, the method further comprises a nanofiltration step after step (c) and/or an ultrafiltration and diafiltration step after the nanofiltration step. In another embodiment of the invention, the method further comprises a low pH inactivation step after step (c), after the nanofiltration step and/or after the ultrafiltration and diafiltration step. In one embodiment of the invention, the method comprises, before step (a), a step of cell culture in a liquid culture medium, preferably in a bioreactor, to provide a liquid culture medium containing the protein. The cultured cells may be mammalian, bacterial or yeast cells.

The invention therefore also provides an integrated process for the generation of a purified protein from a liquid culture medium.

In certain embodiments of the invention, the first elution buffer comprises 20 mM Bis Tris, and 20 mM NaCl, adjusted to pH 3.7 with acetic acid; the second elution buffer comprises 20 mM Bis Tris, 45 mM NaCl and 25 mM $NH_4Cl$ adjusted to pH 7.25 with acetic acid or comprises 20 mM Bis Tris, 80 mM NaCl and 25 mM $NH_4Cl$ adjusted to pH 6.2 with acetic acid; the equilibration buffer comprises 20 mM Bis Tris, and 20 mM NaCl, adjusted to pH 7.4 with acetic acid; and the wash buffer comprises 20 mM Bis Tris, and 1 M NaCl adjusted to pH 7.4 with acetic acid. In other embodiments of the invention, the sanitation buffer comprises 0.1 N sodium hydroxide.

The invention provides a kit comprising a multi-modal resin or cation-exchange chromatography matrix, a Protein A matrix and/or an anion-exchange chromatography matrix; and at least one buffer comprising or consisting of Bis Tris, acetic acid, NaCl, water, and optionally $NH_4Cl$. In some embodiments, the kit is used for purifying a protein from solution using a method of the invention.

In one embodiment, the kit comprises a multi-modal resin chromatography column, a Protein A column and/or an anion-exchange chromatography column; and at least one buffer comprising or consisting of Bis Tris, acetic acid, NaCl, water, and optionally $NH_4Cl$.

In another embodiment, the kit comprises a cation-exchange membrane adsorber, a Protein A membrane adsorber and/or an anion-exchange membrane adsorber; and at least one buffer comprising or consisting of Bis Tris, acetic acid, NaCl, water, and optionally $NH_4Cl$.

The invention also provides a kit comprising a multi-modal resin or cation-exchange chromatography matrix, a Protein A matrix and/or an anion-exchange chromatography matrix; and instructions for preparing at least one buffer comprising or consisting of Bis Tris, acetic acid, NaCl, water, and optionally $NH_4Cl$. In some embodiments, the kit is used for purifying a protein from solution using a method of the invention.

In one embodiment, the kit comprises a multi-modal resin chromatography column, a Protein A column and/or an anion-exchange chromatography column; and instructions for preparing at least one buffer comprising or consisting of Bis Tris, acetic acid, NaCl, water, and optionally $NH_4Cl$.

In another embodiment, the kit comprises a cation-exchange membrane adsorber, a Protein A membrane adsorber and/or an anion-exchange membrane adsorber; and instructions for preparing at least one buffer comprising or consisting of Bis Tris, acetic acid, NaCl, water, and optionally $NH_4Cl$.

The invention further provides a method for preparing equilibration buffer comprising creating a 100 L solution with a final concentration of 20 mM Bis Tris and 20 mM NaCl; adjusting the pH of the solution to 7.4 with acetic acid; and collecting 25 L of the solution. The invention also provides a method for preparing wash buffer comprising collecting 25 L of the remaining 75 L of solution from the preparation of the equilibration buffer and adding e.q. 1 M NaCl to these 25 L of solution. The invention further provides a method for preparing an elution buffer comprising collecting 25 L of the remaining 50 L of solution from the preparation of the equilibration buffer and adjusting the pH of these 25 L of solution to 3.7 with acetic acid. The invention further provides a method for preparing an elution buffer comprising adding e.q. 45 mM NaCl and e.q. 25 mM $NH_4Cl$ to the remaining 25 L of solution from the preparation of the equilibration buffer and adjusting the pH of these 25 L to 7.25 with acetic acid. The buffers prepared by the methods disclosed herein can be used for purifying a protein from solution using a method of the invention.

Also provided herein are isolated proteins, pharmaceutical agents and pharmaceutical compositions obtained by any of the methods described herein.

These and other features and advantages of the disclosed purification method will be more fully understood from the following detailed description taken together with the accompanying claims. It is noted that the scope of the claims is defined by the recitations therein and not by the specific discussion of features and advantages set forth in the description.

In the context of the invention, the terms "comprising", "having", "including" and "containing" are to be construed as open-ended terms (i.e., meaning "including, but not limited to,") unless otherwise noted. Additionally, the term "comprising" encompasses "consisting" (e.g., a composition "comprising" X may consist exclusively of X or may include something additional, e.g., X+Y).

BRIEF DESCRIPTION OF DRAWINGS

The following detailed description of the embodiments of the disclosed purification method can be best understood when read in conjunction with the following drawings.

DETAILED DESCRIPTION OF ASPECTS AND EMBODIMENTS

Figure 1:
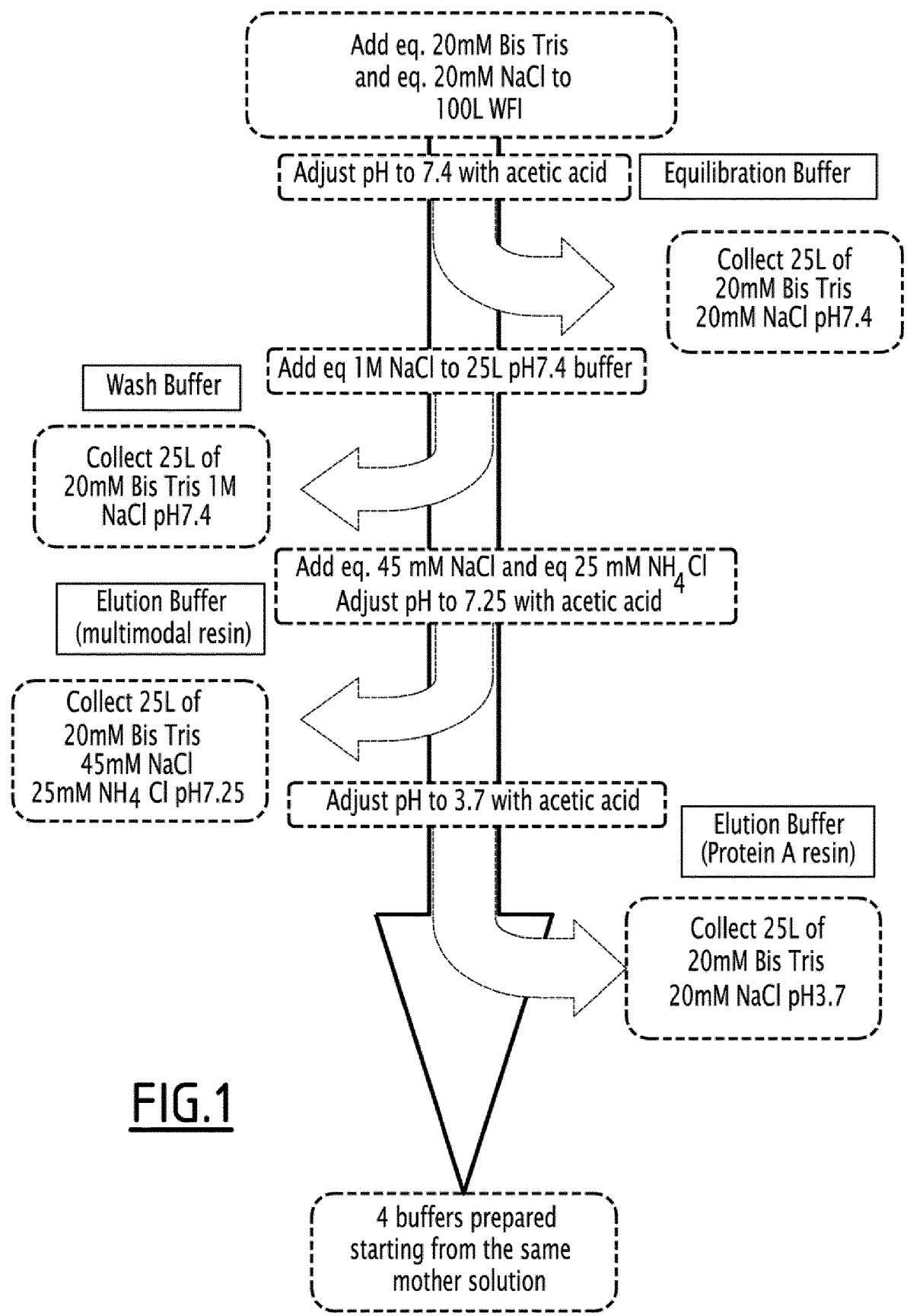
FIG. 1 shows a schematic of the protocol used to formulate the buffers of the purification method disclosed in Examples 2 to 7.

Based on the availability of mixed mode resins (also called multi-modal resins) and chromatography membrane adsorbers, the inventors have developed a new purification process using only three chromatography steps. In other terms, the method comprises only three steps involving a passage over a chromatography matrix.

The invention pertains to a method for purifying a protein from solution comprising or consisting of:
(a) a first chromatography step comprising:
    passing said solution over a first chromatography matrix;
    eluting a crude protein eluent from the first chromatography matrix using a first elution buffer;
(b) a second chromatography step comprising:
    passing the crude protein eluent obtained at the end of step (a) over a second chromatography matrix;
    eluting a protein eluate from the second chromatography matrix using a second elution buffer; and
(c) a third chromatography step comprising:
    passing the protein eluate obtained at the end of step (b) through a third chromatography matrix in the flow-through mode;
    recovering purified protein from the flow-through of the third chromatography matrix;
wherein each of the buffers comprises Bis Tris.

More specifically, each of the two first above chromatography steps may comprise or consist of:
    passing equilibration buffer over the chromatography matrix;
    passing the solution or the crude protein eluent over the chromatography matrix (as mentioned above);
    passing equilibration buffer over the chromatography matrix;
    optionally passing wash buffer over the chromatography matrix;
    optionally passing equilibration buffer over the chromatography matrix;
    eluting the crude protein eluent or the protein eluate from the chromatography matrix using an elution buffer (as mentioned above),
wherein each of the buffers comprises Bis Tris.

The invention also pertains to a method for purifying a protein from solution comprising or consisting of:
(a) a first chromatography step comprising:
    passing a part of said solution over a first chromatography matrix;
    eluting a crude protein eluent from the first chromatography matrix using a first elution buffer, and
    optionally, passing sanitation buffer over the first chromatography matrix;
(b) a second chromatography step comprising:
    passing the crude protein eluent obtained at the end of step (a) over a second chromatography matrix,
    eluting a protein eluate from the second chromatography matrix using a second elution buffer, and
    optionally, passing sanitation buffer over the second chromatography matrix;

(c) a third chromatography step comprising:
  passing the protein eluate obtained at the end of step (b) through a third chromatography matrix in the flow-through mode,
  recovering purified protein from the flow-through of the third chromatography matrix, and
  optionally passing sanitation buffer over the third chromatography matrix;
renewing successively steps (a), (b) and (c) with another part of the solution until all the solution is used, and
collecting the purified proteins recovered at the end of each step (c);
wherein each of the equilibration, wash and elution buffers comprises Bis Tris.

In the context of the invention, the expression "chromatography matrix" refers to any kind of particulate sorbent media, resin or other solid phase, such as a membrane, which, in a purification process, acts as the absorbent to separate the molecule to be purified from other molecules present in a mixture. The matrix, in particular matrices consisting of resins, can be in the form of columns, or in the form of membrane adsorbers.

In the context of the invention, a "membrane adsorber" refers to a flat sheet of acrylic polymer, bearing ionic groups and comprising attached functional groups such as affinity groups and ionic exchange groups. One of the differences between resin and membrane is the flow distribution: by diffusion for resin and by convection in membranes.

In one embodiment of the method of the invention, the first, second and third chromatography matrices are chromatography columns. In another embodiment of the method of the invention, the first, second and third chromatography matrices are chromatography membrane adsorbers.

Accordingly, in one embodiment, the invention pertains to a method for purifying a protein from solution comprising or consisting of:
  (a) a first chromatography step comprising:
    passing said solution over a first chromatography column;
    eluting a crude protein eluent from the first chromatography column using a first elution buffer;
  (b) a second chromatography step comprising:
    passing the crude protein eluent obtained at the end of step (a) over a second chromatography column;
    eluting a protein eluate from the second chromatography column using a second elution buffer; and
  (c) a third chromatography step comprising:
    passing the protein eluate obtained at the end of step (b) through a third chromatography column in the flow-through mode;
    recovering purified protein from the flow-through of the third chromatography column;
wherein each of the buffers comprises Bis Tris.

More specifically, each of the two first above chromatography steps may comprise or consist of:
  passing equilibration buffer over the chromatography column;
  passing the solution or the crude protein eluent over the chromatography column (as mentioned above);
  passing equilibration buffer over the chromatography column;
  optionally passing wash buffer over the chromatography column;
  optionally passing equilibration buffer over the chromatography column;
  eluting the crude protein eluent or the protein eluate from the chromatography column using an elution buffer (as mentioned above),
wherein each of the buffers comprises Bis Tris.

The invention also pertains to a method for purifying a protein from solution comprising or consisting of:
  (a) a first chromatography step comprising:
    passing a part of said solution over a first chromatography column;
    eluting a crude protein eluent from the first chromatography column using a first elution buffer, and
    optionally, passing sanitation buffer over the first chromatography column;
  (b) a second chromatography step comprising:
    passing the crude protein eluent obtained at the end of step (a) over a second chromatography column,
    eluting a protein eluate from the second chromatography column using a second elution buffer, and
    optionally, passing sanitation buffer over the second chromatography column;
  (c) a third chromatography step comprising:
    passing the protein eluate obtained at the end of step (b) through a third chromatography column in the flow-through mode,
    recovering purified protein from the flow-through of the third chromatography column, and
    optionally passing sanitation buffer over the third chromatography column;
renewing successively steps (a), (b) and (c) with another part of the solution until all the solution is used, and
collecting the purified proteins recovered at the end of each step (c);
wherein each of the equilibration, wash and elution buffers comprises Bis Tris.

In another embodiment, the invention pertains to a method for purifying a protein from solution comprising or consisting of:
  (a) a first chromatography step comprising:
    passing said solution over a first chromatography membrane adsorber;
    eluting a crude protein eluent from the first chromatography membrane adsorber using a first elution buffer;
  (b) a second chromatography step comprising:
    passing the crude protein eluent obtained at the end of step (a) over a second chromatography membrane adsorber;
    eluting a protein eluate from the second chromatography membrane adsorber using a second elution buffer; and
  (c) a third chromatography step comprising:
    passing the protein eluate obtained at the end of step (b) through a third chromatography membrane adsorber in the flow-through mode;
    recovering purified protein from the flow-through of the third chromatography membrane adsorber;
wherein each of the buffers comprises Bis Tris.

More specifically, each of the two first above chromatography steps may comprise or consist of:
  passing equilibration buffer over the chromatography membrane adsorber;
  passing the solution or the crude protein eluent over the chromatography membrane adsorber (as mentioned above);
  passing equilibration buffer over the chromatography membrane adsorber;

optionally passing wash buffer over the chromatography membrane adsorber;

optionally passing equilibration buffer over the chromatography membrane adsorber;

eluting the crude protein eluent or the protein eluate from the chromatography membrane adsorber using an elution buffer (as mentioned above), wherein each of the buffers comprises Bis Tris.

The invention also pertains to a method for purifying a protein from solution comprising or consisting of:

(a) a first chromatography step comprising:
passing a part of said solution over a first chromatography membrane adsorber;
eluting a crude protein eluent from the first chromatography membrane adsorber using a first elution buffer, and
optionally, passing sanitation buffer over the first chromatography membrane adsorber;

(b) a second chromatography step comprising:
passing the crude protein eluent obtained at the end of step (a) over a second chromatography membrane adsorber,
eluting a protein eluate from the second chromatography membrane adsorber using a second elution buffer, and
optionally, passing sanitation buffer over the second chromatography membrane adsorber;

(c) a third chromatography step comprising:
passing the protein eluate obtained at the end of step (b) through a third chromatography membrane adsorber in the flow-through mode,
recovering purified protein from the flow-through of the third chromatography membrane adsorber, and
optionally passing sanitation buffer over the third chromatography membrane adsorber;

renewing successively steps (a), (b) and (c) with another part of the solution until all the solution is used, and collecting the purified proteins recovered at the end of each step (c);

wherein each of the equilibration, wash and elution buffers comprises Bis Tris.

As indicated above, the above method of the invention only comprises three chromatography steps. Even though the method according to the invention only comprises three chromatography steps, it allows obtaining purified proteins that are suitable for pharmaceutical purposes and in particular for administration to human beings.

In addition to the absence of human handling in the purification process (and consequent reduction in the overall time required to complete the purification process), the disclosed method reduces the amount of buffers and resins used for purification. In addition, the main buffers comprise the same components (i.e. Bis Tris, NaCl, acetic acid, water and optionally $NH_4Cl$), which greatly facilitates buffer preparation. The disclosed purification method also simplifies mAb purification, improves the overall yield, and reduces raw materials, storage facilities, cost of goods and process time, in addition to allowing for the purification of a variety of mAbs.

In contrast with conventional protein purification methods, as stated above, the method disclosed herein uses four or five buffers: an equilibrium buffer, a wash buffer, two elution buffers, and optionally a sanitation buffer. The four main buffers used in the disclosed method are made with the same matrix of compounds, from a mother solution, which largely facilitates buffer preparation.

As used herein, "buffers according to the invention" refer to buffers comprising Bis Tris. Bis Tris is a compound well known to the skilled in the art, the IUPAC name of which is 2-[bis(2-hydroxyethyl)amino]-2-(hydroxymethyl)propane-1,3-diol, and the CAS Number of which is 6976-37-0. Such buffers according to the invention may correspond to an equilibrium buffer, to a wash buffer, and/or to an elution buffer.

More specifically, such buffers according to the invention may comprise or consist of varying concentrations of the same chemicals (one of them being Bis Tris). In a specific embodiment, the buffers comprise or consist of Bis Tris, acetic acid and water. In a more specific embodiment, the buffers comprise or consist of Bis Tris, acetic acid, NaCl, water, and optionally $NH_4Cl$. In other terms, such buffers comprise or consist of varying concentrations of Bis Tris, acetic acid, NaCl, water and optionally $NH_4Cl$.

The elution buffer may for example comprise or consist of 15 to 25 mM (e.g. 20 mM) Bis Tris, and 15 to 25 mM (e.g. 20 mM) NaCl, adjusted to a pH comprised between 3 and 4 (e.g. 3.7) with acetic acid. Such an elution buffer is notably suitable for use with an affinity chromatography matrix, in particular with an affinity chromatography column or membrane adsorber, such as a Protein A matrix, in particular a Protein A column or a Protein A membrane adsorber.

The elution buffer may also comprise or consist of 15 to 25 mM (e.g. 20 mM) Bis Tris, 40 to 50 mM (e.g. 45 mM) NaCl, and 20 to 30 mM (e.g. 25 mM) $NH_4Cl$, adjusted to a pH comprised between 7 and 8 (e.g. 7.25) with acetic acid. Such an elution buffer is notably for use with a multi-modal resin chromatography matrix, in particular with a multi-modal resin chromatography column, such as e.g. Capto MMC.

The elution buffer may also comprise or consist of 15 to 25 mM (e.g. 20 mM) Bis Tris, 50 to 150 mM (e.g. 80 mM) NaCl, and 20 to 30 mM (e.g. 25 mM) $NH_4Cl$, adjusted to a pH comprised between 6 and 7 (e.g. 6.2) with acetic acid. Such an elution buffer is notably for use with a cation-exchange chromatography matrix, in particular with a cation-exchange membrane adsorber.

The equilibration buffer may comprise or consist of 15 to 25 mM (e.g. 20 mM) Bis Tris, and 15 to 25 mM (e.g. 20 mM) NaCl, adjusted to a pH comprised between 7 and 8 (e.g. 7.4) with acetic acid.

The wash buffer may comprise or consist of 15 to 25 mM (e.g. 20 mM) Bis Tris, and 0.9 to 1.1 M (e.g. 1 M) NaCl adjusted to a pH comprised between 7 and 8 (e.g. 7.4) with acetic acid.

More specifically, one equilibration buffer for use in the disclosed method contains 20 mM Bis Tris and 20 mM NaCl, adjusted to pH 7.4 with 2 mM acetic acid. One wash buffer for use in the disclosed method contains 20 mM Bis Tris and 1 M NaCl, adjusted to pH 7.4 with 2 mM acetic acid. A first elution buffer for use in the disclosed method contains 20 mM Bis Tris and 20 mM NaCl, adjusted to pH 3.7 with 275 mM acetic acid. A second elution buffer for use in the disclosed method contains 20 mM Bis Tris, 45 mM NaCl, and 25 mM $NH_4Cl$ adjusted to pH 7.25 with 5 mM acetic acid, in particular for use with a multi-modal resin chromatography column, or contains 20 mM Bis Tris, 80 mM NaCl, and 25 mM $NH_4Cl$ adjusted to pH 6.2 with 5 mM acetic acid, in particular for use with a cation-exchange membrane adsorber.

Advantages of the above buffer formulations include the capability for a mAb product to pass through the three chromatography matrices, in particular the three chromatography columns or the three chromatography membrane adsorbers, used in the disclosed method with larger compatibility, while minimizing undesired interactions, limiting pH and conductivity drops, and promoting increased yield versus traditional purification methods. In addition to using a reduced number of buffers, another aspect of the disclosed method is the use of a Bis-Tris buffer. The use of such a buffer avoids adjusting pH between the three chromatographic steps and thus enables running the method in a closed system from harvest to the last purification step.

The sanitation buffer optionally used in the context of the invention may comprise or consist of 0.05 N to 0.15 N (e.g. 0.1 N) NaOH. Such a sanitation buffer is notably suitable for use with an affinity chromatography matrix, in particular with an affinity chromatography column such as Protein A column or with an affinity chromatography membrane adsorber such as Sartobind Protein A membrane adsorber, with a multi-modal resin or cation-exchange chromatography matrix, in particular with a multi-modal resin chromatography column, such as Capto MMC, or with a cation-exchange chromatography membrane adsorber, such as Sartobind S membrane adsorber, and/or with an anion-exchange chromatography matrix, in particular with an anion-exchange chromatography column, such as BioPro Q75, or with an anion-exchange chromatography membrane adsorber, such as Sartobind Q membrane adsorber.

The terms "polypeptide" or "protein" as used herein refer to:

1) molecules having the sequence of native proteins, that is a) proteins produced by naturally-occurring and specifically non-recombinant cells, or b) genetically-engineered or recombinant cells, or 2) molecules differing from the sequence of native proteins by deletions from, additions to, and/or substitutions of one or more amino acids and/or by at least one post-translational modification (e.g. glycosylation).

The molecules mentioned in the paragraph 1) above may be called native proteins.

The molecules mentioned in the paragraph 2) above are non-natural proteins.

In certain aspects, the protein to be purified is an antibody.

The term "antibody" as used herein refers to an intact antibody, or a binding fragment thereof that competes with the intact antibody for specific binding. Binding fragments include, but are not limited to, F(ab), F(ab'), F(ab')$_2$, Fv, and single-chain antibodies. The term "heavy chain" includes any immunoglobulin polypeptide having sufficient variable region sequence to confer specificity for an antigen.

The term "heavy chain" as used herein encompasses a full-length heavy chain and fragments thereof. A full-length heavy chain includes a variable region domain, VH, and three constant region domains, CH1, CH2, and CH3. The VH domain is at the amino-terminus of the polypeptide, and the CH3 domain is at the carboxyl-terminus.

The term "light chain" as used herein encompasses a full-length light chain and fragments thereof. A full-length light chain includes a variable region domain, VL, and a constant region domain, CL. Like the heavy chain, the variable region domain of the light chain is at the amino-terminus of the polypeptide. The term "light chain" as used herein includes any immunoglobulin polypeptide having sufficient variable region sequence to confer specificity for an antigen.

Naturally occurring antibody structural units typically comprise a tetramer. Each such tetramer typically is composed of two identical pairs of polypeptide chains, each pair having one full-length light chain (typically having a molecular weight of about 25 kDa) and one full-length heavy chain (typically having a molecular weight of about 50-70 kDa). The amino-terminal portion of each light and heavy chain typically includes a variable region of about 100 to 110 or more amino acids that typically is responsible for antigen recognition. The carboxy-terminal portion of each chain typically defines a constant region responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, typically, the variable and constant regions are joined by a "J" region of about 12 or more amino acids, with the heavy chain also including a "D" region of about 10 more amino acids.

The variable regions of each light/heavy chain pair typically form the antigen-binding site. The variable regions typically exhibit the same general structure of relatively conserved framework regions (FR) joined by three hyper-variable regions, also called complementarity determining regions or CDRs. The CDRs from the two chains of each pair typically are aligned by the framework regions, which may enable binding to a specific epitope. From N-terminal to C-terminal, both light and heavy chain variable regions typically comprise the domains FR1, CDR1, FR2, CDR2, FR3, CDR3, and FR4. The assignment of amino acids to each domain is typically in accordance with the definitions of Kabat et al., 1991, Sequences of Proteins of Immunological Interest, 5th ed., U.S. Department of Health and Human Services, NIH Publication No. 91-3242. A bispecific or bifunctional antibody typically is an artificial hybrid antibody having two different heavy chain/light chain pairs and two different binding sites.

A F(ab) fragment is comprised of one light chain and the CH1 and variable regions of one heavy chain. The heavy chain of a F(ab) molecule cannot form a disulfide bond with another heavy chain molecule. A F(ab') fragment contains one light chain and one heavy chain that contains more of the constant region, between the CH1 and CH2 domains, such that an interchain disulfide bond can be formed between two heavy chains to form an F(ab')$_2$ molecule. The Fv region comprises the variable regions from both the heavy and light chains, but lacks the constant regions. Single-chain antibodies are Fv molecules in which the heavy and light chain variable regions have been connected by a flexible linker to form a single polypeptide chain, which forms an antigen-binding region. A bivalent antibody other than a "multispecific" or "multifunctional" antibody, in certain embodiments, is understood to comprise binding sites having identical antigenic specificity.

Monoclonal antibodies (mAbs) that can be purified by the disclosed method can be produced by a variety of techniques, including conventional monoclonal antibody methodology, e.g., the standard somatic cell hybridization technique well known in the art. Although somatic cell hybridization procedures are preferred, in principle, other techniques for producing monoclonal antibodies can be employed, e.g., viral or oncogenic transformation of B-lymphocytes. The monoclonal antibody may for instance correspond to a murine, a chimeric, a humanized or a fully human antibody.

In a specific embodiment, the antibody purified by the method of the invention is a monoclonal antibody selected from the group consisting of an antibody that specifically binds to the protofibrillar form of the human β-amyloid protein (e.g. a humanized antibody), an antibody that specifically binds to the bacterial surface polysaccharide poly-N-acetyl glucosamine (PNAG) (e.g. a fully human antibody), an antibody that specifically binds to Carcinoembryonic antigen-related cell adhesion molecule 5 (CEACAM5) and an antibody that specifically binds to the CD38 transmembrane glycoprotein (e.g. a humanized antibody).

Non-limiting examples of antibodies that may be purified by the method of the invention also comprise: panitumumab, omalizumab, abagovomab, abciximab, actoxumab, adalimumab, adecatumumab, afelimomab, afutuzumab, alacizumab, alemtuzumab, alirocumab, altumomab, amatuximab, anatumomab, apolizumab, atinumab, tocilizumab, basilizimab, bectumomab, belimumab, bevacizumab, biciromab, canakinumab, cetuximab, daclizumab, densumab, eculizumab, edrecolomab, efalizumab, efungumab, ertumaxomab, etaracizumab, etanercept, golimumab, infliximab, natalizumab, palivizumab, panitumumab, pertuzumab, ranibizumab, rituximab, tocilizumab, trastuzumab, dupilumab, sarilumab or fresolimumab.

In certain aspects, the protein to be purified is an enzyme. Non-limiting examples of enzymes that may be purified by the method of the invention comprise acid α-glucosidase, α-L-iduronidase, iduronate sulfatase, heparan N-sulfatase, galactose-6-sulfatase, acid β-galactosidase, β-glucoronidase, N-acetylglucosamine-1-phosphotransferase, α-N-acetylgalactosaminidase (α-galactosidase B), acid lipase, lysosomal acid ceramidase, acid sphingomyelinase, β-glucosidase, galactosylceramidase, α-galactosidase A, acid β-galactosidase, β-galactosidase, neuraminidase, hexosaminidase A or hexosaminidase B.

Other non-limiting examples of proteins that may be purified by the method of the invention comprise human erythropoietin, tumor necrosis factor (e.g. TNF-α, TNF-β or TNF-K), interferon alpha or interferon beta.

The solution containing the protein to be purified may be a culture medium, preferably a clarified culture medium. The solution containing the protein to be purified is for example a culture medium obtained in a perfusion bioreactor or fed-batch bioreactor.

Examples of perfusion bioreactors or fed-batch bioreactors are disclosed in U.S. provisional patent application No. 61/775,060 (herein incorporated by reference in its entirety).

The term "clarified culture medium" means a liquid culture medium obtained from a mammalian, bacterial or yeast cell culture that is substantially free (e.g., at least 80%, 85%, 90%, 92%, 94%, 96%, 98%, or 99% free) of mammalian, bacteria or yeast cells.

The phrase "recovering the protein" as used herein refers to collecting a protein after using the disclosed purification method. The disclosed purification method can be achieved using a variety of standard protein chromatography techniques, such as, but not limited to, affinity chromatography, ion exchange chromatography, hydrophobic interaction chromatography, gel filtration chromatography, and multi-modal resin chromatography.

In certain embodiments of the disclosed method, the first chromatography matrix is a Protein A matrix. In particular embodiments of the disclosed method, the first chromatography matrix is a Protein A column. In other particular embodiments of the disclosed method, the first chromatography matrix is a Protein A membrane adsorber. The Protein A matrix, in particular the Protein A column or the Protein A membrane adsorber, functions via affinity between the resin ligand and the protein, resulting in high efficiency removal of impurities. Another advantage of using a Protein A matrix, in particular of using a Protein A column or a Protein A membrane adsorber, in the disclosed method is that mAbs have universal affinity toward Protein A. In one embodiment of the disclosed method, the Protein A column is MabSelect Sure resin (GE Healthcare). In another embodiment of the disclosed method, the Protein A column is Absolute High Cap (Novasep). In one embodiment of the disclosed method, the Protein A membrane adsorber is Sartobind Protein A membrane adsorber (Sartorius).

In additional embodiments of the disclosed method, the second chromatography matrix is a multi-modal (mixed-mode) resin or cation-exchange chromatography matrix. In particular embodiments of the disclosed method, the second chromatography matrix is a multi-modal (mixed-mode) resin chromatography column. The multi-modal resin interacts with the protein of interest through several mechanisms with mAb:ionic, hydrophobic and hydrogen bond interactions. More specifically, in a multi-modal resin chromatography column, the mAb:ionic interaction is a mAb:cationic interaction, as opposed to mAb:anionic interactions that occur in a classical anion exchange chromatography (AEX) column.

In one specific embodiment of the disclosed method, the multi-modal resin is Capto MMC resin (GE Healthcare). Capto MMC is a multimodal cation exchanger with a highly cross-linked agarose base matrix. The characteristics of Capto MMC are summarized below (see GE Healthcare Life Sciences, data file 11-0035-45 AA).

| | |
|---|---|
| Matrix | highly cross-linked agarose |
| Functional group | multimodal weak cation exchanger |
| Total ionic capacity | 0.07-0.09 mmol H$^+$/ml medium |
| Particle size | 75 μm (d50v) |
| Flow velocity | at least 600 cm/h in a 1 m diameter column with 20 cm bed height at 20° C. using process buffers with the same viscosity as water at <3 bar (0.3 MPa). |
| Dynamic binding | >45 mg BSA/ml medium at 30 mS/cm |
| pH-stability | |
| short-term | 2 to 14 |
| long-term | 2 to 12 |
| Working temperature | +4° C. to +30° C. |

In other particular embodiments of the disclosed method, the second chromatography matrix is a cation-exchange membrane adsorber.

In one other specific embodiment of the disclosed method, the cation-exchange membrane adsorber is Sartobind S membrane adsorber (Sartorius). In another specific embodiment of the disclosed method, the cation-exchange membrane adsorber is NatriPur HD-C membrane adsorber (Natrix).

In additional embodiments of the disclosed method, the third chromatography matrix is an anion-exchange chromatography matrix. In particular embodiments of the disclosed method, the third chromatography matrix is an anion-exchange chromatography column.

In other particular embodiments of the disclosed method, the third chromatography matrix is an anion-exchange membrane adsorber. The positively-charged organic moiety covalently cross-linked to an inert polymeric support of the anion-exchange matrix, in particular of the anion-exchange resin, interacts with the protein of interest through mAb:anionic interactions. In one embodiment of the disclosed method, the anion-exchange chromatography column is BioPro Q75 (YMC). The characteristics of BioPro Q75 are summarized below (see YMC-BioPro Q75 & S75 data sheet).

| Matrix | hydrophilic polymer beads |
|---|---|
| Charged group | —$CH_2N^+(CH_3)_3$ |
| Ion exchange capacity | 0.13 meq/ml resin |
| Particle size | 75 μm |
| Linear velocity | 3.0 cm/min (180 cm/h) |
| Dynamic binding | 187 mg/ml resin |
| pH range | 2.0-12.0 |

In another embodiment of the disclosed method, the anion-exchange membrane adsorber is Sartobind Q membrane adsorber (Sartorius). In another embodiment of the disclosed method, the anion-exchange membrane adsorber is Sartobind STIC membrane adsorber (Sartorius). In another embodiment of the disclosed method, the anion-exchange membrane adsorber is HD-Q membrane adsorber (Natrix).

In one embodiment, the method according to the invention does not comprise adjusting the pH of the crude protein eluent and/or of the protein eluate at the end of the first chromatographic step and/or at the end of the second chromatographic step.

In a particular embodiment, the crude protein eluent obtained at the end of the first chromatographic step is directly passed over the second chromatography matrix, in particular over the second chromatography column or membrane adsorber. More specifically, no treatment (such as pH adjustment, buffer exchange or dilution) is then carried out between the two steps. In such a method, the multi-modal resin chromatography column may for instance correspond to a Capto MMC column. In such a method, the cation-exchange membrane adsorber may for instance correspond to a Sartobind S membrane adsorber. Additionally, in a particular embodiment, the protein eluate obtained at the end of the second chromatographic step is directly passed through the third chromatography matrix, in particular through the third chromatography column or membrane adsorber. More specifically, no treatment (such as pH adjustment, buffer exchange or dilution) is then carried out between the two steps. In such a method, the multi-modal resin chromatography column may for instance correspond to a Capto MMC column and/or the anion-exchange chromatography column may for instance correspond to a Bio-Pro Q75 column. A specific example of this method is disclosed in Example 4. In such a method, the cation-exchange membrane adsorber may for instance correspond to a Sartobind S membrane adsorber and/or the anion-exchange chromatography membrane adsorber may for instance correspond to a Sartobind Q membrane adsorber. A specific example of this method is disclosed in Example 8.

In such a method, inter-step treatments requiring manual intervention and opening of the purification system (e.g., dilution in an inactivation vessel, post inactivity filtration and pH adjustment in a Protein A pool vessel) are totally absent.

A chromatography matrix used in the present methods can be a reduced bioburden chromatography matrix (e.g., a gamma-irradiated chromatography matrix). Examples of reduced bioburden chromatography matrix are disclosed in U.S. provisional patent application 61/928,906 that is herein incorporated by reference in its entirety.

The method of the invention may thus be performed in a MCCS comprising a first, second and third chromatography matrices.

The term "multi-column chromatography system" or "MCCS" means a system of a total of two or more interconnected or switching chromatography columns and/or chromatographic membranes. A non-limiting example of a multi-column chromatography system is a periodic counter current chromatography system (PCCS) containing a total of two or more interconnected or switching chromatography columns and/or chromatographic membranes. Additional examples of multi-column chromatography systems are described herein and are known in the art.

The chromatography column(s) and/or chromatographic membrane(s) present in a MCCS can be connected or moved with respect to each other by a switching mechanism (e.g., a column-switching mechanism). The MCCS can also include one or more (e.g., two, three, four, or five) pumps (e.g., automated, e.g., automated peristaltic pumps). The column-switching events can be triggered by the detection of a level of the protein to be purified detected by UV absorbance corresponding to a certain level of protein in the fluid passing through the MCCS (e.g., the input into and/or eluate from one or more of the chromatography column(s) and/or chromatographic membranes in the MCCS), a specific volume of liquid (e.g., buffer), or specific time elapsed. Column switching generally means a mechanism by which at least two different chromatography columns and/or chromatographic membranes in a MCCS (e.g., two or more different chromatography columns and/or chromatographic membranes present in a MCCS are allowed to pass through a different step (e.g., equilibration, loading, eluting, or washing) at substantially the same time during at least part of the process.

The chromatography column(s) and/or the chromatographic membrane(s) present in a MCCS can have one or more of any of the exemplary shapes, sizes, volumes (bed volumes), and/or unit operation(s) described herein.

The chromatography column(s) and/or the chromatographic membrane(s) present in a MCCS can contain one or more of any of the exemplary resins described herein or known in the art. For example, the resin contained in one or more of the chromatography column(s) and/or chromatographic membrane(s) present in the MCCS can be a resin that utilizes a capture mechanism (e.g., protein A-binding capture mechanism, protein G-binding capture mechanism, antibody- or antibody fragment-binding capture mechanism, substrate-binding capture mechanism, cofactor-binding capture mechanism, an aptamer-binding capture mechanism, and/or a tag-binding capture mechanism). The resin contained in one or more of the chromatography column(s) and/or chromatographic membrane(s) of the MCCS can be a cation exchange resin, an anion exchange resin, a molecular sieve resin, or a hydrophobic interaction resin, or any combination thereof. Additional examples of resins that can be used to purify a protein are known in the art, and can be contained in one or more of the chromatography column(s) and/or chromatographic membrane(s) present in MCCS. The chromatography column(s) and/or chromatography membranes present in the MCCS can contain the same and/or different resins (e.g., any of the resins described herein or known in the art for use in recombinant protein purification).

The chromatography column(s) and/or chromatographic resin(s) present in the MCCS can perform one or more unit operations (e.g., capturing a protein, purifying a protein, polishing a protein, inactivating viruses, adjusting the ionic concentration and/or pH of a fluid containing the protein, or filtering a fluid containing a protein). In non-limiting examples, the MCCS can perform the unit operations of capturing a protein from a fluid (e.g., a liquid culture medium) and inactivating viruses present in the fluid containing the recombinant therapeutic protein. The MCCS can perform any combinations of two of more unit operations described herein or known in the art.

A MCCS can be equipped with: one or more (e.g., two, three, four, five, six, seven, eight, nine, or ten) UV monitors, one or more (e.g., two, three, four, five, six, seven, eight, nine, or ten) valves, one or more (e.g., two, three, four, five, six, seven, eight, nine, or ten) pH meters, and/or one or more (e.g., two, three, four, five, six, seven, eight, nine, or ten) conductivity meters. A MCCS can also be equipped with an operating system that utilizes software (e.g., Unicorn-based software, GE Healthcare, Piscataway, N.J.) for sensing when a column-switching should occur (e.g., based upon UV absorbance, volume of liquid, or time elapsed) and affecting (triggering) the column-switching events. In the examples where MCCS includes one or more UV detectors, the UV detectors can be placed optionally at the inlet of one or more (e.g., two, three, four, five, six, seven, eight, nine, or ten) of the chromatography column(s) and/or chromatographic membrane(s) in the MCCS, and/or at the outlet of one or more of the chromatography column(s) and/or chromatography membrane(s) in the MCCS.

A MCCS can further include one or more (e.g., two, three, four, five, six, seven, eight, nine, ten, eleven, twelve, thirteen, fourteen, fifteen, sixteen, seventeen, eighteen, nineteen, twenty, twenty-one, twenty-two, twenty-three, or twenty-four) in-line buffer adjustment reservoir(s) and/or a buffer reservoir(s). In other examples, the MCCS can include one or more (e.g., two, three, four, five, or six) break tanks that can hold fluid that cannot readily pass into one or more of the chromatography columns and/or chromatographic membranes in the MCCS. The systems described herein can contain one or more break tanks. Other examples of the systems described herein do not include a break tank.

A MCCS may include an inlet through which fluid (e.g., a liquid culture medium that is substantially free of cells) can be passed into said MCCS. The inlet can be any structure known in the art for such purposes. It can include, e.g., a threading, ribbing, or a seal that allows for a fluid conduit to be inserted, such that after insertion of the fluid conduit into the inlet, fluid will enter the MCCS through the inlet without significant seepage of fluid out of the inlet. Non-limiting inlets that can be used in the present systems are known and would be understood by those in the art. Some examples of the systems provided herein also include a bioreactor that is in fluid connectivity with the inlet of the MCCS. Any of the exemplary bioreactors described herein or known in the art can be used in the present systems.

The MCCS may include an outlet through which the protein can exit the system. The outlet can include, e.g., a threading, ribbing, or a seal that allows for a fluid conduit to be inserted or a vial designed to contain or store the protein. An outlet can contain a surface that can be used to seal a sterile vial or other such storage container onto the outlet in order to allow the protein to flow directly into the sterile vial or storage container. Non-limiting outlets that can be used in the present systems are known and would be understood by those in the art.

Some examples of the systems provided herein also include a pump system. A pump system can include one or more the following: one or more (e.g., two, three, four, five, six, seven, eight, nine, or ten) pumps (e.g., any of the pumps described herein or known in the art), one or more (e.g., two, three, four, or five) filters (e.g., any of the filters described herein or known in the art), one or more (e.g., two, three, four, five, six, seven, eight, nine, or ten) UV detectors, and one or more (e.g., two, three, four, or five) break tanks.

Some examples of the systems described herein further include a further fluid conduit connected to the fluid conduit between the pump and the inlet of the MCCS, where one end of the further fluid conduit is fluidly connected to a bioreactor and the other end is fluidly connected to the fluid conduit between the pump and the inlet. This further fluid conduit can include a filter that is capable of removing cells from the liquid culture medium removed from the bioreactor (e.g., ATF cell retention system). In some examples, this particular fluid conduit can include one or more (e.g., two, three, or four) pumps (e.g., any of the pumps described herein or known in the art) and/or one or more (e.g., two, three, or four) break tanks (e.g., any of the exemplary break tanks described herein), where these pump(s) and/or break tank(s) are in fluid connection with the fluid present in the fluid conduit.

The systems described herein can optionally include a fluid conduit disposed between the final chromatography column or chromatographic membrane and the outlet. The systems described herein can further include one or more filters in fluid connection with the fluid conduit disposed between the final chromatography column or chromatographic membrane in and the outlet, such that the filter can remove, e.g., precipitated material, particulate matter, or bacteria from the fluid present in the fluid conduit disposed between the final chromatography column or chromatographic membrane in the MCCS and the outlet.

The method of the invention can be run in continuous mode. In other words, the method of the invention can be a continuous method for purifying a protein from solution.

The term "continuous method" or "method in a continuous mode" means a method which continuously feeds fluid through at least a part of the system.

By the term "fluid", it is meant herein any liquid, such as a solution containing the protein to be purified, a buffer or a low or acidic pH solution for viral inactivation.

In a preferred embodiment, the first, second and third matrices are continuously fed through with a fluid.

The term "integrated process" means a process which is performed using structural elements that function cooperatively to achieve a specific result (e.g. the generation of a purified protein from a liquid culture medium).

Examples of integrated process are disclosed in U.S. provisional patent application No. 61/775,060 (herein incorporated by reference in its entirety).

The scale-up of the method of the invention may also include the use of column-switching and/or increasing the bed volume of each chromatography column.

Furthermore, the method of the invention can be run in a closed system from the first step of the method to the last one. In particular, the chromatography steps and the optionally filtration step(s) (for example, the nanofiltration step and/or the ultrafiltration and diafiltration step) can be run in a closed system. In a specific embodiment of the method of the invention, the solution comprising proteins is passed, parts by parts, over the three chromatography matrices, in particular over the three chromatography columns or membrane adsorbers, each passage of a part of the solution corresponding to a run. The proteins recovered at the end of each run are then collected and pooled. Specific examples of this method are disclosed in Examples 5, 6 and 8. In such a method, the column or the membrane adsorber of a chromatography step is used several times, and optionally sanitated using for example a sanitation buffer as defined above, thereby enabling reducing the amount of resin or membrane adsorber devices, and buffer needed. For instance, a sequence of 3 to 50 runs (e.g. 3 to 30 runs, 5 to 25 runs, 10 to 20 runs, or 15 runs) can be performed continuously. More specifically, 3, 4, 5, 6, 7 or 8 runs can be performed in continuous mode, followed by sanitation of the 3 columns or membrane adsorbers (e.g. using the sanitation buffer). This might be repeated e.g. 2, 3, 4, 5, 6, 7, 8, 9, 10 or more times.

The method disclosed herein can be used to recover purified proteins. As used herein, "purified" refers to a purity that allows for the effective use of the protein in vitro, ex vivo, or in vivo. For a protein to be useful in in vitro, ex vivo, or in vivo applications, it should be substantially free of contaminants, other proteins, and/or chemicals that could interfere with the use of that protein in such applications, or that at least would be undesirable for inclusion with the protein of interest. Such applications include that preparation of therapeutic compositions, the administration of the protein in a therapeutic composition, and other methods disclosed herein. Preferably, a "purified" protein, as referenced herein, is a protein that can be produced by any method (i.e., by direct purification from a natural source, recombinantly, or synthetically), and that has been purified from other protein components such that the protein comprises at least about 80% weight/weight of the total protein in a given composition, and more preferably, at least about 85%, and more preferably at least about 90%, and more preferably at least about 91%, and more preferably at least about 92%, and more preferably at least about 93%, and more preferably at least about 94%, and more preferably at least about 95%, and more preferably at least about 96%, and more preferably at least about 97%, and more preferably at least about 98%, and more preferably at least about 99% weight/weight of the total protein in a given composition.

As used herein, "crude protein" refers to a protein that can be produced by any method (i.e., by direct purification from a natural source, recombinantly, or synthetically), and that has been purified from other protein components such that the protein comprises less than about 80% weight/weight of the total protein in a given composition.

In a particular embodiment, the method for purifying a protein from solution according to the invention comprises:
(a) a first chromatography step comprising:
   (i) passing equilibration buffer over a Protein A column;
   (ii) passing the solution over the Protein A column;
   (iii) passing equilibration buffer over the Protein A column;
   (iv) passing wash buffer over the Protein A column;
   (v) passing equilibration buffer over the Protein A column; and
   (vi) eluting a crude protein eluent from the Protein A column using a first elution buffer;
(b) a second chromatography step comprising:
   (i) passing equilibration buffer over a multi-modal resin chromatography column;
   (ii) passing the crude protein eluent from step (a) over the multi-modal resin chromatography column;
   (iii) passing equilibration buffer over the multi-modal resin chromatography column; and
   (iv) eluting a protein eluate from the multi-modal resin chromatography column using a second elution buffer;
(c) a third chromatography step comprising:
   (i) passing equilibration buffer over an anion-exchange chromatography column;
   (ii) passing the protein eluate from step (b) over the anion-exchange chromatography column in the flow-through mode; and
   (iii) recovering purified protein from the flow-through of the anion-exchange chromatography column,
wherein the equilibration buffer comprises 15 to 25 mM Bis Tris, and 15 to 25 mM NaCl, adjusted to a pH comprised between 7 and 8 with acetic acid, the wash buffer comprises of 15 to 25 mM Bis Tris, and 0.9 to 1.1 M NaCl adjusted to a pH comprised between 7 and 8 with acetic acid, the first elution buffer comprises 15 to 25 mM Bis Tris, and 15 to 25 mM NaCl, adjusted to a pH comprised between 3 and 4 with acetic acid and the second elution buffer comprises 15 to 25 mM Bis Tris, 40 to 50 mM NaCl, and 20 to 30 mM $NH_4Cl$, adjusted to a pH comprised between 7 and 8 with acetic acid.

In another embodiment, the method for purifying a protein from solution according to the invention comprises:
(a) a first chromatography step comprising:
   (i) passing equilibration buffer over a Protein A column;
   (ii) passing a part of the solution over the Protein A column;
   (iii) passing equilibration buffer over the Protein A column;
   (iv) passing wash buffer over the Protein A column;
   (v) passing equilibration buffer over the Protein A column; and
   (vi) eluting a crude protein eluent from the Protein A column using a first elution buffer;
(b) a second chromatography step comprising:
   (i) passing equilibration buffer over a multi-modal resin chromatography column;
   (ii) passing the crude protein eluent from step (a) over the multi-modal resin chromatography column;
   (iii) passing equilibration buffer over the multi-modal resin chromatography column; and
   (iv) eluting a protein eluate from the multi-modal resin chromatography column using a second elution buffer;
(c) a third chromatography step comprising:
   (i) passing equilibration buffer over an anion-exchange chromatography column;
   (ii) passing the protein eluate from step (b) over the anion-exchange chromatography column in the flow-through mode; and
   (iii) recovering purified protein from the flow-through of the anion-exchange chromatography column,
(d) renewing successively steps a), b) and c) with another part of the solution until all the solution is used, and
(e) collecting the purified proteins recovered at the end of each third chromatography step;
wherein the equilibration buffer comprises 15 to 25 mM Bis Tris, and 15 to 25 mM NaCl, adjusted to a pH comprised between 7 and 8 with acetic acid, the wash buffer comprises of 15 to 25 mM Bis Tris, and 0.9 to 1.1 M NaCl adjusted to a pH comprised between 7 and 8 with acetic acid, the first elution buffer comprises 15 to 25 mM Bis Tris, and 15 to 25 mM NaCl, adjusted to a pH comprised between 3 and 4 with acetic acid and the second elution buffer comprises 15 to 25 mM Bis Tris, 40 to 50 mM NaCl, and 20 to 30 mM $NH_4Cl$, adjusted to a pH comprised between 7 and 8 with acetic acid.

In another particular embodiment, the method for purifying a protein from solution according to the invention comprises:
(a) a first chromatography step comprising:
   (i) passing equilibration buffer over a Protein A membrane adsorber;
   (ii) passing the solution over the Protein A membrane adsorber;

(iii) passing equilibration buffer over the Protein A membrane adsorber;
(iv) passing wash buffer over the Protein A membrane adsorber;
(v) passing equilibration buffer over the Protein A membrane adsorber; and
(vi) eluting a crude protein eluent from the Protein A membrane adsorber using a first elution buffer;
(b) a second chromatography step comprising:
(i) passing equilibration buffer over a cation-exchange membrane adsorber;
(ii) passing the crude protein eluent from step (a) over the cation-exchange membrane adsorber;
(iii) passing equilibration buffer over the cation-exchange membrane adsorber; and
(iv) eluting a protein eluate from the cation-exchange membrane adsorber using a second elution buffer;
(c) a third chromatography step comprising:
(i) passing equilibration buffer over an anion-exchange membrane adsorber;
(ii) passing the protein eluate from step (b) over the anion-exchange membrane adsorber in the flow-through mode; and
(iii) recovering purified protein from the flow-through of the anion-exchange membrane adsorber,
wherein the equilibration buffer comprises 15 to 25 mM Bis Tris, and 15 to 25 mM NaCl, adjusted to a pH comprised between 7 and 8 with acetic acid, the wash buffer comprises of 15 to 25 mM Bis Tris, and 0.9 to 1.1 M NaCl adjusted to a pH comprised between 7 and 8 with acetic acid, the first elution buffer comprises 15 to 25 mM Bis Tris, and 15 to 25 mM NaCl, adjusted to a pH comprised between 3 and 4 with acetic acid and the second elution buffer comprises 15 to 25 mM Bis Tris, 50 to 150 mM NaCl, and 20 to 30 mM $NH_4Cl$, adjusted to a pH comprised between 6 and 7 with acetic acid.

In another embodiment, the method for purifying a protein from solution according to the invention comprises:
(a) a first chromatography step comprising:
(i) passing equilibration buffer over a Protein A membrane adsorber;
(ii) passing a part of the solution over the Protein A membrane adsorber;
(iii) passing equilibration buffer over the Protein A membrane adsorber;
(iv) passing wash buffer over the Protein A membrane adsorber;
(v) passing equilibration buffer over the Protein A membrane adsorber; and
(vi) eluting a crude protein eluent from the Protein A membrane adsorber using a first elution buffer;
b) a second chromatography step comprising:
(i) passing equilibration buffer over a cation-exchange membrane adsorber;
(ii) passing the crude protein eluent from step (a) over the cation-exchange membrane adsorber;
(iii) passing equilibration buffer over the cation-exchange membrane adsorber; and
(iv) eluting a protein eluate from the cation-exchange membrane adsorber using a second elution buffer;
(c) a third chromatography step comprising:
(i) passing equilibration buffer over an anion-exchange membrane adsorber;
(ii) passing the protein eluate from step (b) over the anion-exchange membrane adsorber in the flow-through mode; and
(iii) recovering purified protein from the flow-through of the anion-exchange membrane adsorber,
(d) renewing successively steps a), b) and c) with another part of the solution until all the solution is used, and
(e) collecting the purified proteins recovered at the end of each third chromatography step;
wherein the equilibration buffer comprises 15 to 25 mM Bis Tris, and 15 to 25 mM NaCl, adjusted to a pH comprised between 7 and 8 with acetic acid, the wash buffer comprises of 15 to 25 mM Bis Tris, and 0.9 to 1.1 M NaCl adjusted to a pH comprised between 7 and 8 with acetic acid, the first elution buffer comprises 15 to 25 mM Bis Tris, and 15 to 25 mM NaCl, adjusted to a pH comprised between 3 and 4 with acetic acid and the second elution buffer comprises 15 to 25 mM Bis Tris, 50 to 150 mM NaCl, and 20 to 30 mM $NH_4Cl$, adjusted to a pH comprised between 6 and 7 with acetic acid.

The method for purifying a protein from solution may comprise at least one filtration step, such as a nanofiltration step, an ultrafiltration step and/or a diafiltration step. The filtration step(s) may be performed before and/or after the chromatographic steps. When purifying recombinant proteins for pharmaceutical purposes, the chromatographic steps are typically followed by filtration steps. Therefore, the method of the invention may further comprise a nanofiltration step after step (c). An ultrafiltration and diafiltration step may further be carried out after the nanofiltration step. As used herein, "ultrafiltration" or "UF" refers to a filtration technique using a semi-permeable membrane to physically and selectively remove particles and/or ions from a solution based on particle size and size of the pores in the UF membrane. As used herein, "nanofiltration" refers to filtration of a solution through a nanofilter that is used to remove, e.g., viral particles. As used herein, "diafiltration" refers a technique that uses ultrafiltration membranes to completely remove, replace, or lower the concentration of salts or solvents from solutions.

The method of the invention may also further comprise at least one viral inactivation step. Said at least one viral inactivation step may be performed at any stage of the method of the invention, for example before step (a), after step (a), after step (b), after step (c), after the nanofiltration step and/or after the ultrafiltration and diafiltration step. Such a viral inactivation step may typically be a low or acidic pH inactivation step. As used herein, "low or acidic pH inactivation" refers to a viral inactivation technique using acidic pH to denature viruses, in particular enveloped viruses. Typically, the low or acidic pH inactivation step is carried out by incubating the recovered proteins at a pH of between about 3.0 to 5.0 (e.g., between about 3.5 to about 4.5, between about 3.5 to about 4.25, between about 3.5 to about 4.0, for example 4.0) for a period of at least 30 minutes (e.g., a period of between 1 hour to 21 days, a period of between about 2 hours to 21 days, or a period of between about 4 hours to 21 days). For example, the low or acidic pH inactivation step is carried out by incubating the recovered proteins at a pH of 4 during for example 6 h to 21 days.

The method of the invention may also comprise, before step (a), a step of providing a liquid culture medium containing the protein to be purified that is substantially free of cells, wherein said liquid culture medium is fed into the first chromatography matrix.

For example, the method of the invention for purifying a protein from solution may comprise:
(pre-a) a step of providing a liquid culture medium containing the protein to be purified that is substantially free of cells,
(a) a first chromatography step comprising:
passing said liquid culture medium of step (pre-a) over a first chromatography matrix;

eluting a crude protein eluent from the first chromatography matrix using a first elution buffer;
(b) a second chromatography step comprising:
passing the crude protein eluent obtained at the end of step (a) over a second chromatography matrix;
eluting a protein eluate from the second chromatography matrix using a second elution buffer; and
(c) a third chromatography step comprising:
passing the protein eluate obtained at the end of step (b) through a third chromatography matrix in the flow-through mode;
recovering purified protein from the flow-through of the third chromatography matrix;
wherein each of the buffers comprises Bis Tris.

Finally, the purified protein may be formulated into a composition suitable for storage, and/or into a pharmaceutical composition suitable for administration to animals and/or humans.

One of the numerous advantages of the disclosed method is that it allows obtaining good yields of highly pure protein. The purified protein that is recovered with the method of the invention can for instance exhibit a purity of at least 95%, 96%, 97%, 98%, 99%, 99.2%, 99.5%, or 99.9%. More particularly, one of the numerous advantages of the disclosed method is that it allows obtaining solutions of highly pure protein containing reduced amounts of contaminating DNA, of high molecular weight (HMW) species (which correspond to protein aggregates) and/or of host cell proteins (HCP). The solution comprising purified protein that is recovered with the method of the invention can for instance exhibit an amount of contaminating DNA of less than 0.4 ppb, less than 0.3 ppb, less than 0.2 ppb or less than 0.1 ppb. The solution comprising purified protein that is recovered with the method of the invention can also for instance exhibit a concentration of HMW species of less than 0.9%, less than 0.8%, less than 0.7%, less than 0.6%, less than 0.5% or less than 0.4%. The solution comprising purified protein that is recovered with the method of the invention can also for instance exhibit a concentration of HCP of less than 23 ppm, less than 22 ppm, less than 21 ppm, less than 20 ppm, less than 19 ppm or less than 18 ppm. In addition, the method of the invention can allow recovering the purified protein with a yield of at least 85%, 90%, 95%, 96%, 97%, 98% or 99%. Another aspect of the invention pertains to a method for preparing buffers suitable for use in the method of the invention. Indeed, all these buffers can very easily and rapidly be prepared starting from a single mother solution.

Such a method for preparing buffers may comprise or consist of the steps of:
i) creating a solution (e.g. a solution of 100 L) with a final concentration of 15 to 25 mM (e.g. 20 mM) Bis Tris and of 15 to 25 mM (e.g. 20 mM) NaCl;
ii) adjusting the pH of the solution to a value comprised between 7 and 8 (e.g. 7.4) with acetic acid;
iii) collecting one fourth of the solution, thereby obtaining an equilibration buffer;
iv) adjusting the pH of one fourth of the remaining three fourth of solution from step (iii) to a value comprised between 3 and 4 (e.g. 3.7) with acetic acid, thereby obtaining an elution buffer;
v) collecting one fourth of the remaining two fourth of solution from step (iii), adding NaCl to obtain a final NaCl concentration comprised between 40 and 50 mM (e.g. 45 mM), further adding $NH_4Cl$ to obtain a final $NH_4Cl$ concentration comprised between 20 and 30 mM (e.g. 25 mM), and adjusting the pH to a value comprised between 7 and 8 (e.g. 7.25) with acetic acid, thereby obtaining a further elution buffer;
vi) adding NaCl to the remaining one fourth of solution from step (iii) and adding NaCl to obtain a final NaCl concentration comprised between 0.9 to 1.1 M (e.g. 1 M), thereby obtaining a wash buffer.

Such a method is schematically depicted on FIG. 1.

Another method for preparing buffers may comprise or consist of the steps of:
i) creating a solution (e.g. a solution of 100 L) with a final concentration of 15 to 25 mM (e.g. 20 mM) Bis Tris and of 15 to 25 mM (e.g. 20 mM) NaCl;
ii) adjusting the pH of the solution to a value comprised between 7 and 8 (e.g. 7.4) with acetic acid;
iii) collecting one fourth of the solution, thereby obtaining an equilibration buffer;
iv) adjusting the pH of one fourth of the remaining three fourth of solution from step (iii) to a value comprised between 3 and 4 (e.g. 3.7) with acetic acid, thereby obtaining an elution buffer;
v) collecting one fourth of the remaining two fourth of solution from step (iii), adding NaCl to obtain a final NaCl concentration comprised between 70 and 90 mM (e.g. 80 mM), further adding $NH_4Cl$ to obtain a final $NH_4Cl$ concentration comprised between 20 and 30 mM (e.g. 25 mM), and adjusting the pH to a value comprised between 6 and 7 (e.g. 6.2) with acetic acid, thereby obtaining a further elution buffer;
vi) adding NaCl to the remaining one fourth of solution from step (iii) and adding NaCl to obtain a final NaCl concentration comprised between 0.9 to 1.1 M (e.g. 1 M), thereby obtaining a wash buffer.

The above method for preparing buffers may also correspond to the very first step of the method of the invention, before performing the three chromatographic steps.

The invention further pertains to a kit comprising or consisting of:
(a) a multi-modal resin or cation-exchange chromatography matrix, an affinity chromatography matrix such as a Protein A matrix, and/or an anion-exchange chromatography matrix; and
(b) at least one buffer according to the invention (e.g. comprising or consisting of Bis Tris, acetic acid, NaCl, water, and optionally $NH_4Cl$), and/or instructions for preparing at least one buffer according to the invention (e.g. comprising or consisting of Bis Tris, acetic acid, NaCl, water, and optionally $NH_4Cl$).

In one embodiment, the kit comprises or consists of:
(a) a multi-modal resin chromatography column, an affinity chromatography column such as a Protein A column, and/or an anion-exchange chromatography column; and
(b) at least one buffer according to the invention (e.g. comprising or consisting of Bis Tris, acetic acid, NaCl, water, and optionally $NH_4Cl$), and/or instructions for preparing at least one buffer according to the invention (e.g. comprising or consisting of Bis Tris, acetic acid, NaCl, water, and optionally $NH_4Cl$).

In another embodiment, the kit comprises or consists of:
(a) a cation-exchange membrane adsorber, an affinity chromatography membrane adsorder such as a Protein A membrane adsorber, and/or an anion-exchange chromatography membrane adsorber; and (b) at least one buffer according to the invention (e.g. comprising or consisting of Bis Tris, acetic acid, NaCl, water, and optionally $NH_4Cl$), and/or instructions for preparing at least one buffer according to the invention (e.g. comprising or consisting of Bis Tris, acetic acid, NaCl, water, and optionally $NH_4Cl$).

EXAMPLES

The Examples that follow are illustrative of specific embodiments of the disclosed method, and various uses thereof. They are set forth for explanatory purposes only, and should not be construed as limiting the scope of the invention in any way.

Example 1: Optimization of Purification Buffers

Bis Tris buffers can advantageously be used as buffers with a multi-modal resin chromatography column.

The crude protein eluent obtained after passage through a Protein A chromatography column was passed through a Capto MMC multi-modal resin chromatography column.

This resin is able to fix mAb even at low pH, like those obtained after a chromatography step on a Protein A column. However, this resin also needs salt to obtain a good elution. Nevertheless, a too high concentration of salt is detrimental for mAb stability, since it increases the level of high molecular weight (HMW) species in eluted samples, and is too efficient on impurities fixed on medium, leading to a decreased purity of mAb.

To avoid these drawbacks, the inventors made a design of experiment (DOE) in order to reduce salt concentration and pH in the elution buffer of step (a).

To this end, the inventors introduced a new kind of salt, ammonium chloride, which brings the same conductivity as NaCl but is stronger in terms of interactions than Nat.

DOE Parameters

A central composite face design (CCF) was applied for optimization of elution conditions with MODDE 9 software (UMETRICS). The CCF design was composed of a full factorial design and three center points (in all 17 experiments). Elution pH was varied between 7.2 and 7.8, and in the same way NaCl concentration was varied from 0 to 100 mM and $NH_4Cl$ concentration was varied from 0 to 50 mM.

Factors and responses are summarized below.

DOE Experiments

The 17 experiments are summarized in the table below.

| Exp No | Exp name | Conditions | | | Preparation (250 mL) | | |
|---|---|---|---|---|---|---|---|
| | | pH | Na (mM) | $NH_4$ (mM) | pH | NaCl (mg) | $MH_4Cl$ (mg) |
| 1 | N1 | 7.2 | 0 | 0 | 7.2 | 0 | 0 |
| 2 | N2 | 7.8 | 0 | 0 | 7.8 | 0 | 0 |
| 3 | N3 | 7.2 | 100 | 0 | 7.2 | 1.461 | 0 |
| 4 | N4 | 7.8 | 100 | 0 | 7.8 | 1.461 | 0 |
| 5 | N5 | 7.2 | 0 | 50 | 7.2 | 0 | 0.67 |
| 6 | N6 | 7.8 | 0 | 50 | 7.8 | 0 | 0.67 |
| 7 | N7 | 7.2 | 100 | 50 | 7.2 | 1.461 | 0.67 |
| 8 | N8 | 7.8 | 100 | 50 | 7.8 | 1.461 | 0.67 |
| 9 | N9 | 7.2 | 50 | 25 | 7.2 | 0.73 | 0.334 |
| 10 | N10 | 7.8 | 50 | 25 | 7.8 | 0.73 | 0.334 |
| 11 | N11 | 7.5 | 0 | 25 | 7.5 | 0 | 0.334 |
| 12 | N12 | 7.5 | 100 | 25 | 7.5 | 1.761 | 0.334 |
| 13 | N13 | 7.5 | 50 | 0 | 7.5 | 0.73 | 0 |
| 14 | N14 | 7.5 | 50 | 50 | 7.5 | 0.73 | 0.67 |
| 15 | N15 | 7.5 | 50 | 25 | 7.5 | 0.73 | 0.334 |
| 16 | N16 | 7.5 | 50 | 25 | 7.5 | 0.73 | 0.334 |
| 17 | N17 | 7.5 | 50 | 25 | 7.5 | 0.73 | 0.334 |

DOE Results

It appeared during the runs that four experiments were inconsistent in terms of products recovery. N1 and N2 runs had no elution due to conditions and during N5 and N11 runs, elution had to be stopped after 10 column volumes (CV). These experiments were thus excluded from the analysis.

All the experiments were submitted to SEC-HPLC and HCP analysis.

The results are summarized in the table below.

| Exp No | Exp name | Run order | Incl/Excl | pH | Na | $NH_4$ | Yield | HCP | HMW |
|---|---|---|---|---|---|---|---|---|---|
| 1 | N1 | 17 | Excl | 7.2 | 0 | 0 | 0 | 0 | 0 |
| 2 | N2 | 9 | Excl | 7.8 | 0 | 0 | 0 | 0 | 0 |
| 3 | N3 | 4 | Incl | 7.2 | 100 | 0 | 99.8 | 25 | 1.5 |
| 4 | N4 | 3 | Incl | 7.8 | 100 | 0 | 94.9 | 42 | 1.84 |
| 5 | N5 | 14 | Excl | 7.2 | 0 | 50 | 14.6 | 98 | 0.19 |
| 6 | N6 | 6 | Incl | 7.8 | 0 | 50 | 92.2 | 73 | 0.52 |
| 7 | N7 | 8 | Incl | 7.2 | 100 | 50 | 99.1 | 34 | 1.94 |
| 8 | N8 | 16 | Incl | 7.8 | 100 | 50 | 98.5 | 45 | 1.96 |

| Factors | | | | | | | | |
|---|---|---|---|---|---|---|---|---|
| Name | Units | Type | Use | Settings | Transf. | Prec. | MLR scale | PLS scale |
| pH | pHu | Quant. | Control. | 7.2 to 7.8 | None | Free | Orthog. | Unit Var. |
| Na | mM | Quant. | Control. | 0 to 100 | None | Free | Orthog. | Unit Var. |
| $NH_4$ | mM | Quant. | Control. | 0 to 50 | None | Free | Orthog. | Unit Var. |

| Responses | | | | | | | |
|---|---|---|---|---|---|---|---|
| Name | Units | Transf. | MLR scale | PLS scale | Type | Min | Target | Max |
| Yield | % | None | None | Unit Var. | Regular | 0 | 95 | 100 |
| HCP | ppm | None | None | Unit Var. | Regular | 0 | 50 | 80 |
| HMW | % | None | None | Unit Var. | Regular | 0 | 0.7 | 1 |

Abbreviations:

Quant.: quantitative; Control.: controlled; Transf.: transformation; Prec.: precision; MLR: multiple linear regression; Orthog.: orthogonal; PLS: partial least squares; Unit Var.: unit variance; HCP: host cell protein; HMW: high molecular weight species -continued

| Exp No | Exp name | Run order | Incl/Excl | pH | Na | NH$_4$ | Yield | HCP | HMW |
|---|---|---|---|---|---|---|---|---|---|
| 9 | N9 | 5 | Incl | 7.2 | 50 | 25 | 95.6 | 25 | 0.76 |
| 10 | N10 | 15 | Incl | 7.8 | 50 | 25 | 96.7 | 68 | 1.65 |
| 11 | N11 | 1 | Excl | 7.5 | 0 | 25 | 0.5 | 4370 | 0 |
| 12 | N12 | 2 | Incl | 7.5 | 100 | 25 | 99.4 | 35 | 1.98 |
| 13 | N13 | 13 | Incl | 7.5 | 50 | 0 | 87.4 | 38 | 0.43 |
| 14 | N14 | 7 | Incl | 7.5 | 50 | 50 | 97.5 | 39 | 1.72 |
| 15 | N15 | 11 | Incl | 7.5 | 50 | 25 | 97.2 | 39 | 1.22 |
| 16 | N16 | 12 | Incl | 7.5 | 50 | 25 | 98.6 | 39 | 1.21 |
| 17 | N17 | 10 | Incl | 7.5 | 50 | 25 | 95.8 | 42 | 1.21 |

In the MODDE 9.0 prediction tool, the inventors determined the sweet spot, meaning the space containing conditions to apply, by fixing the following responses:
yield: 95 to 100%
HCP: 20 to 30 ppm
HMW: 0.4 to 0.8%

Figure 2:
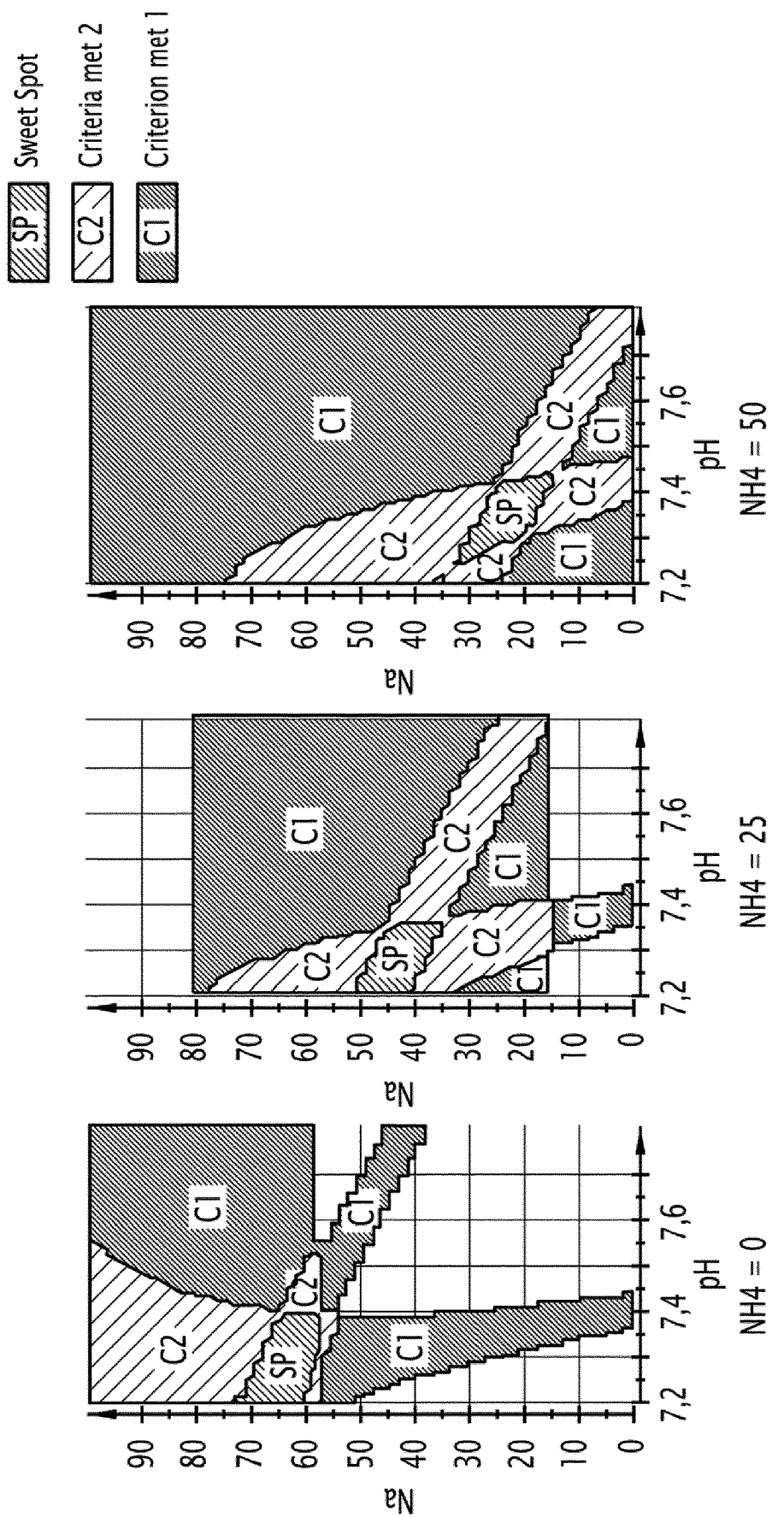
FIG. 2 shows graphs representing the sweet spots for the second elution buffer for three $NH_4Cl$ concentrations.

The sweet spots are represented on FIG. 2 for three kinds of NH$_4$Cl concentration (0, 25 and 50 mM).

The black space is the space containing the first criterion met: a yield between 90 and 100%. The light grey space is the space containing both yield and HCP rate (20 to 30 ppm). The dark grey space is the sweet spot which is the space containing the 3 criteria met: yield, HCP rate and HMW rate (0.4 to 0.8%).

The inventors thus demonstrated, with this graphical description, that the more NaCl was used, the more HMW and yield were increasing. Additionally, the more pH was increased, the more HCP rate was important. Accordingly, the inventors demonstrated that, to obtain a high yield, with a good purity, the elution had to be performed at low pH and with a low NaCl concentration.

The inventors demonstrated that NH$_4$Cl could be used to decrease NaCl concentration. The most appropriate NH$_4$Cl concentration was 25 mM, giving a sweet spot with more than 95% of yield, a HCP rate around 30 ppm and a HMW rate of 0.6%.

The inventors thus demonstrated that the optimal elution buffer for the second chromatography step was 20 mM Bis Tris, 45 mM NaCl, 25 mM NH$_4$Cl, qsp acetic acid pH 7.25.

Example 2: Optimization of the Third Chromatographic Step

A purification process, in which Sartobind STIC membrane was used as third step, because of its salt tolerant property, in order to polish impurities after the two first chromatographic steps and to remove viruses, was initially designed.

However, in a continuous process, each step is carried out a plenty of times. Disposable membranes, such as Sartobind STIC membranes, cannot be re-used. The inventors therefore designed an alternative third chromatographic step enabling polishing impurities, removing viruses and being re-usable, which can thus be used in a continuous process.

Three kinds of media were tested as polishing step:
Sartobind STIC (Sartorius)
Sartobind Q (Sartorius), and
BioPro Q75 (YMC), an AEX resin.

First, the inventors tested these resins after a Capto MMC elution (100 mM NaCl, 20 mM Bis Tris pH 8.0) to evaluate the ability of the third step to remove impurities even with 100 mM NaCl conditions. The Sartobind STIC and Q membranes were evaluated in a single run. The BioPro Q75 was evaluated in three runs: 100 mM, 50 mM and 25 mM NaCl concentration. The results are shown in the table below.

|  | Sartobind STIC | Sartobind Q | BioPro Q75 |
|---|---|---|---|
| Conditions (mM NaCl) | 100 | 100 | 100/50/25 |
| Size (mL) | 0.08 | 0.08 | 2.5 |
| HMW (%) | 1.6 | 1.8 | 1.8/1.7/1.7 |
| HCP (ppm) | 9 | 6 | 20/15/14 |
| DNA (ppb) | 2.8 | 0.01 | 0.1 |

These results thus show that the Sartobind STIC membrane, due to its salt tolerant property, gives good impurities removal. However, an increase of pressure during the run from 1 to 3 bars, shows that it is not possible to use such membranes in a re-usable technology, all the more since the pressure did not decrease after a 1M NaCl wash and after a 0.1 N NaOH sanitation. The best results in terms of impurities were obtained with the Sartobind Q membrane. However, because of re-usability and availability issues, this membrane was considered as not suitable by the inventors.

Finally, the BioPro Q75 resin gave intermediate results in terms of impurities removal. Furthermore, no pressure was observed during the runs. Finally, re-usability was completed because of classical resin technology.

The inventors thus demonstrated that an anion-exchange chromatography column was a good alternative to membrane in polishing steps, in order to carry out protein purification by a continuous process.

Example 3: Formulation of Purification Buffers

The three-step purification method described herein utilizes four buffers: an equilibration buffer, a wash buffer, and two elution buffers, all prepared from the same mother solution. A schematic of the protocol is shown in FIG. 1 and is as follows: eq. 20 mM Bis Tris and eq. 20 mM NaCl were brought up to 100 L water for injection (WFI) as the mother solution, and the pH of the solution was then adjusted to 7.4 using acetic acid. 25 L of the resulting solution was then collected and stored as the equilibration buffer. 25 L of the mother solution was then removed and eq. 1M NaCl was added. This resulting 25 L solution was the wash buffer. The pH of 25 L of the mother solution was then adjusted to 3.7 with acetic acid. This resulting 25 L solution was the first elution buffer. The remaining 25 L of the mother solution was then pH adjusted to 7.25 using acetic acid, and eq. 45 mM NaCl and eq. 25 mM NH$_4$Cl were added, resulting in the other elution buffer.

Example 4: Small Scale Continuous MultiStep Process

The method of the invention was utilized for small-batch purification of a humanized monoclonal antibody that specifically binds to the CD38 transmembrane glycoprotein (anti-CD38 mAb).

Materials and Methods
Material
   First step: 60 mL Absolute High Cap resin in a XK50/20 column customized with Fast Flow tubing
   Second step: 100 mL Capto MMC resin in a XK50/20 column customized with Fast Flow tubing
   Third step: 50 mL BioPro Q75 resin in a XK50/20 column customized with Fast Flow tubing Akta Purifier tubing modified with PEEK tuning i.d. 1.0 mm First Step Details The XK50/20 column was packed with Absolute High Cap resin (Ref. AbSHC 35 P1-A-V-00200). The final volume was 60 mL. HETP was 13538 N/m and asymmetry was 1.2.

Three kinds of buffer were used for this step:
Equilibration buffer made with 20 mM Bis Tris, 2 mM NaCl, qsp acetic acid pH 7.4
Wash buffer made with 20 mM Bis Tris, 1 MNaCl, qsp acetic acid pH 7.4
Elution buffer made with 20 mM Bis Tris, 20 mM NaCl, qsp acetic acid pH 3.7.

The flow rate, according to column size, was set up to 24 mL/min (RT 2.5 min) for equilibration, wash, load and elution step.

Second Step Details

The XK50/20 column was packed with Capto MMC resin (Ref 17-5317-02). The final volume was 100 mL. HETP was 5686 N/m and asymmetry was 1.3.

Two kinds of buffer were used for this step:
Equilibration buffer made with 40 mM Bis Tris, 20 mM NaCl, qsp acetic acid pH 7.4
Elution buffer made with 20 mM Bis Tris, 45 mM NaCl, 25 mM $NH_4Cl$, qsp acetic acid pH 7.25.

The flow rate, according to column size, was set up to 24 mL/min (RT 4.8 min) for equilibration, load and elution step.

Third Step Details

The XK50/20 column was packed with BioPro Q75 resin (Ref QAAOS75). The final volume was 50 mL. HETP was 4875 N/m and asymmetry was 1.6.

One kind of buffer was used for this step:
Equilibration buffer made with 40 mM Bis Tris, 20 mM NaCl, qsp acetic acid pH 7.4.

The flow rate, according to column size, was set up to 24 mL/min (RT 2.1 min) for equilibration and elution step.

Results 2.325 g of bulk harvest (at a concentration of 1.71 g/L) were loaded on Absolute High Cap resin. The total duration to purify the 2,325 g was 2 h 10 min. 2.125 g were recovered meaning that the yield was 91%. Technically, the purification was successfully achieved without back pressure even if the columns were used in a serial configuration.

The impurities removal of the final product obtained with this 3-step process is summarized and compared with the one obtained with the 2-step process described in PCT/EP2012/059528, in the table below.

|  | Bulk harvest | 3-step process final product | 2-step process final product |
| --- | --- | --- | --- |
| Yield (%) |  | 91 | 92 |
| HMW (%) | 8.7 | 0.4 | 0.9 |
| HCP (ppm) | $2.2 \times 10^5$ | 18 | 23 |
| DNA (ppb) | $3 \times 10^6$ | <0.1 | 0.4 |

The inventors thus showed that the new Continuous MultiStep Process was as efficient as the 2-step process described in PCT/EP2012/059528, applied on the same product.

Small scale studies were carried out to evaluate the impurities rate obtained after each step. The inventors showed that every step was efficient to remove impurities, as summarized in the following table.

|  | HMW (%) | HCP (ppm) | DNA (ppb) |
| --- | --- | --- | --- |
| Bulk harvest | 8.7 | $2.2 \times 10^5$ | $3 \times 10^6$ |
| Absolute HC | 1.0 | $1 \times 10^3$ | $2 \times 10^4$ |
| Capto MMC | 0.4 | 40 | 10 |
| BioPro Q75 | 0.4 | 18 | <0.1 |

This example thus shows that the continuous process designed by the inventors is as efficient as a batch process.

Example 5: Full Scale Continuous MultiStep Process

The above method was applied to large-scale purification of a humanized monoclonal antibody that specifically binds to the CD38 transmembrane glycoprotein (anti-CD38 mAb).

Materials and Methods

Materials

First step: 50 mL Absolute High Cap resin with a dynamic binding capacity (DBC) of 50 mg/mL
Second step: 100 mL Capto MMC resin with a DBC of 35 mg/mL
Third step: 50 mL BioPro Q75 resin with a DBC of 170 mg/mL
Periodic Counter Current system from GE (customized Akta purifier), comprising the above 3 columns on line and enabling monitoring of all columns.

Methods

A sequence of 15 runs was performed continuously. More specifically, 5 runs were performed in continuous mode followed by sanitation of the 3 columns, with 0.1N NaOH, before starting a new sequence.

Results

A sequence enabled purifying 10 g of anti-CD38 mAb in less than 500 min.

29.5 g of bulk harvest were loaded and 28 g of purified mAb were recovered. The Continuous Multistep Process of the invention thus enabled reaching an average yield of 95%. These 28 g of purified mAb were obtained in 25 h.

Additionally, the analytical results of the final product were comparable with the ones of the final product obtained with the 2-step process described in PCT/EP2012/059528. These analytical results are summarized in the table below.

|  | Bulk harvest | 2-step process | Continuous Multistep Process |
| --- | --- | --- | --- |
| Yield (%) |  | 94 | 95 |
| HMW (%) | 8.7 | 0.9 | 0.2 |
| HCP (ppm) | $2.2 \times 10^5$ | 4 | 5 |
| DNA (ppb) | $3 \times 10^6$ | 1.3 | <0.1 |

This was also the case when each step was analyzed separately, as shown on the table below.

|  | HMW (%) | HCP (ppm) | DNA (ppb) |
| --- | --- | --- | --- |
| Bulk harvest | 8.7 | $2.2 \times 10^5$ | $3 \times 10^6$ |
| Absolute HC | 1.0 | 800 | $2 \times 10^4$ |
| Capto MMC | 0.2 | 40 | 10 |
| BioPro Q75 | 0.2 | 5 | <0.1 |

Figure 3:
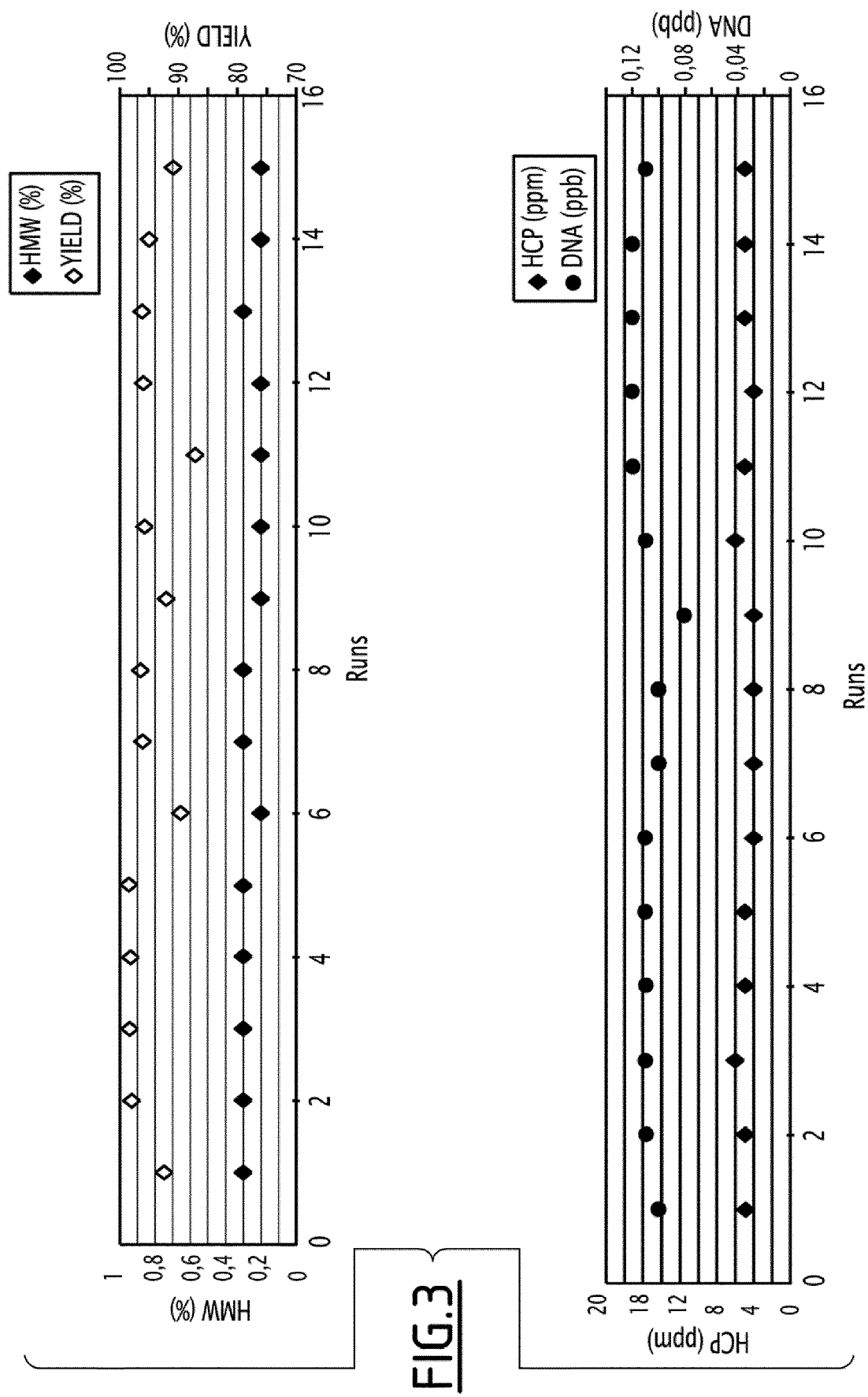
FIG. 3 shows graphs representing the trend analysis of HMW, yield, HCP and DNA in each of the 15 runs of Example 5.

Additionally, as shown in FIG. 3, trends did not show any significant differences between each run.

Example 6: Batch Purification in Continuous Mode

The process described in Example 5 was used to purify anti-CD38 mAb in a full scale continuous batch.

In this example, 43 L of mAb, at a concentration of 1.66 g/L, were purified continuously during 69 h. More specifically, 45 runs were performed, 960 mL of clarified product being loaded in each run. This led to the recovering of 19.5 L of purified mAb, at a concentration of 3.42 g/L, which represents a yield of 93%, using only 70 L of buffers.

The table below summarizes the features of this purification method compared to the ones of a 2-step purification process described in PCT/EP2012/059528.

|  | 2-step process | Continuous multistep process |
|---|---|---|
| Step number | 2 | 3 |
| Run number | 1 + 1 | 45 |
| Duration (h) | 72 | 69 |
| System used | Akta process | Periodic Counter Current system |
| Buffers volume (L) | 99.2 | 69.7 |
| Columns type | BPG140 | XK50/20 |
| Resin volume (L) | 7.5 | 0.2 |

Accordingly, the Continuous MultiStep Process of the invention enables reducing the volume of buffers used of 33% and the volume of resins used of 97%.

Example 7: Purification of Different Monoclonal Antibodies

In addition to the humanized anti-CD38 antibody, the Continuous MultiStep Process described above was used to purify additional antibodies, namely a fully human antibody that specifically binds to the bacterial surface polysaccharide poly-N-acetyl glucosamine (PNAG), a monoclonal antibody that specifically binds to Carcinoembryonic antigen-related cell adhesion molecule 5 (CEACAM5) and the humanized 13C3 mAb which binds to the protofibrillar form of the human β-amyloid protein as described in International Publication No. WO 2009/065054

The table below shows the overall yield and the purity obtained upon purification of these three antibodies.

| Antibody | Overall yield (%)[1] | Purity (%) |
|---|---|---|
| Humanized 13C3 mAb | 86 | 96 |
| Anti-PNAG mAb | 89 | 96 |
| Anti-CD38 mAb | 93 | 99 |
| Anti-CEACAM5 mAb | 92 | 96 |

[1]The overall yield corresponds to the yield before the nanofiltration, ultrafiltration and diafiltration steps.

In conclusion, it has been confirmed with four different antibodies that the Continuous MultiStep Process method allows obtaining good yields of purified antibodies with an excellent degree of purity, the purified antibodies having a quality suitable for administration to human.

Example 8: Membrane Adsorbers Continuous MultiStep Process

The method of the invention using disposable membrane adsorbers was applied to large-scale purification of a humanized monoclonal antibody that specifically binds to CD38 (anti-CD38 mAb).

Materials and Methods

Materials
First step: 4 Sartobind Protein A membrane adsorbers (Sartorius) of 2 mL each
Second step: 2 Sartobind S "nano" membrane adsorbers (Sartorius) of 3 mL each
Third step: 1 Sartobind Q "nano" membrane adsorber (Sartorisu) of 3 mL The buffers used were the same as those described in Example 4, excepted the elution buffer of the second step made with 20 mM Bis Tris, 80 mM NaCl, 25 mM NH$_4$Cl, qsp acetic acid pH 6.2.

Methods

The process was performed to purify 1.5 g of antibodies through 50 runs of 30 mg each over the 3 above steps in a continuous mode.

Briefly, the Protein A membrane adsorber was equilibrated with the equilibration buffer then loaded. After the load, the membrane adsorber was equilibrated again, before the elution with the first elution buffer. The eluate of the Protein A membrane adsorber was directly loaded on the cation-exchange membrane adsorber. While the cation-exchange membrane was equilibrated with the equilibration buffer, the Protein A membrane adsorber was sanitized with the sanitation buffer before a next load. The cation-exchange membrane adsorber was eluted with the second elution buffer and the eluate was directly loaded onto the anion-exchange membrane adsorber.

Results

It was possible to purify the 1.5 g of antibodies in 750 min (15 min by run). The recovery was around 80%.

The analytical results are summarized in the table below.

|  | Membrane Continuous Multistep Process |
|---|---|
| HMW (%) | 1.8 |
| LMW (%) | 0.6 |
| HCP (ppm) | 10 |
| DNA (ppb) | 0.9 |

Accordingly, the Continuous Multistep Process according to the invention, using disposable membrane adsorbers, enable obtaining satisfying impurities removal rates, within internal specifications, without further optimization of the process and buffers compared to the process using re-usable resins.

Figure 4:
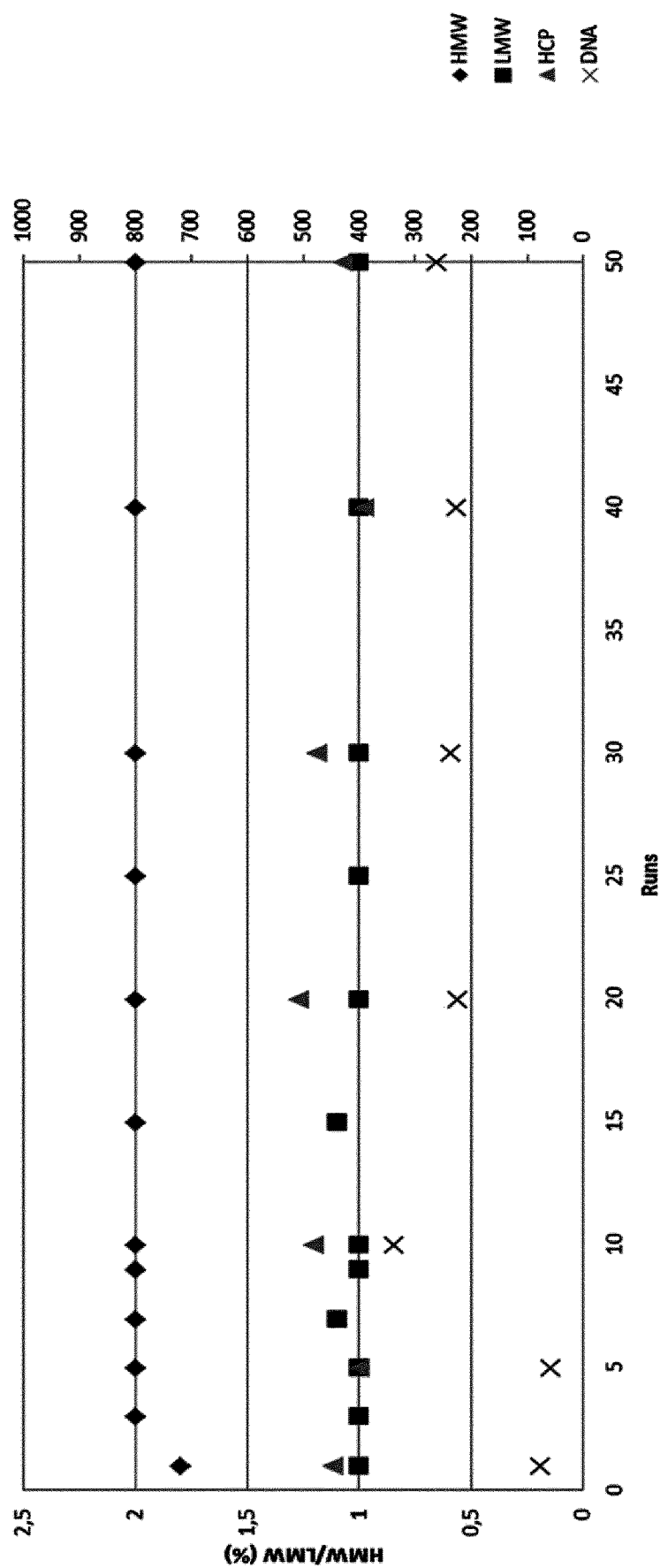
FIG. 4 shows graphs representing the trend analysis of HMW, LMW, HCP and DNA in each of the 50 runs of Example 8.
Figure 5:
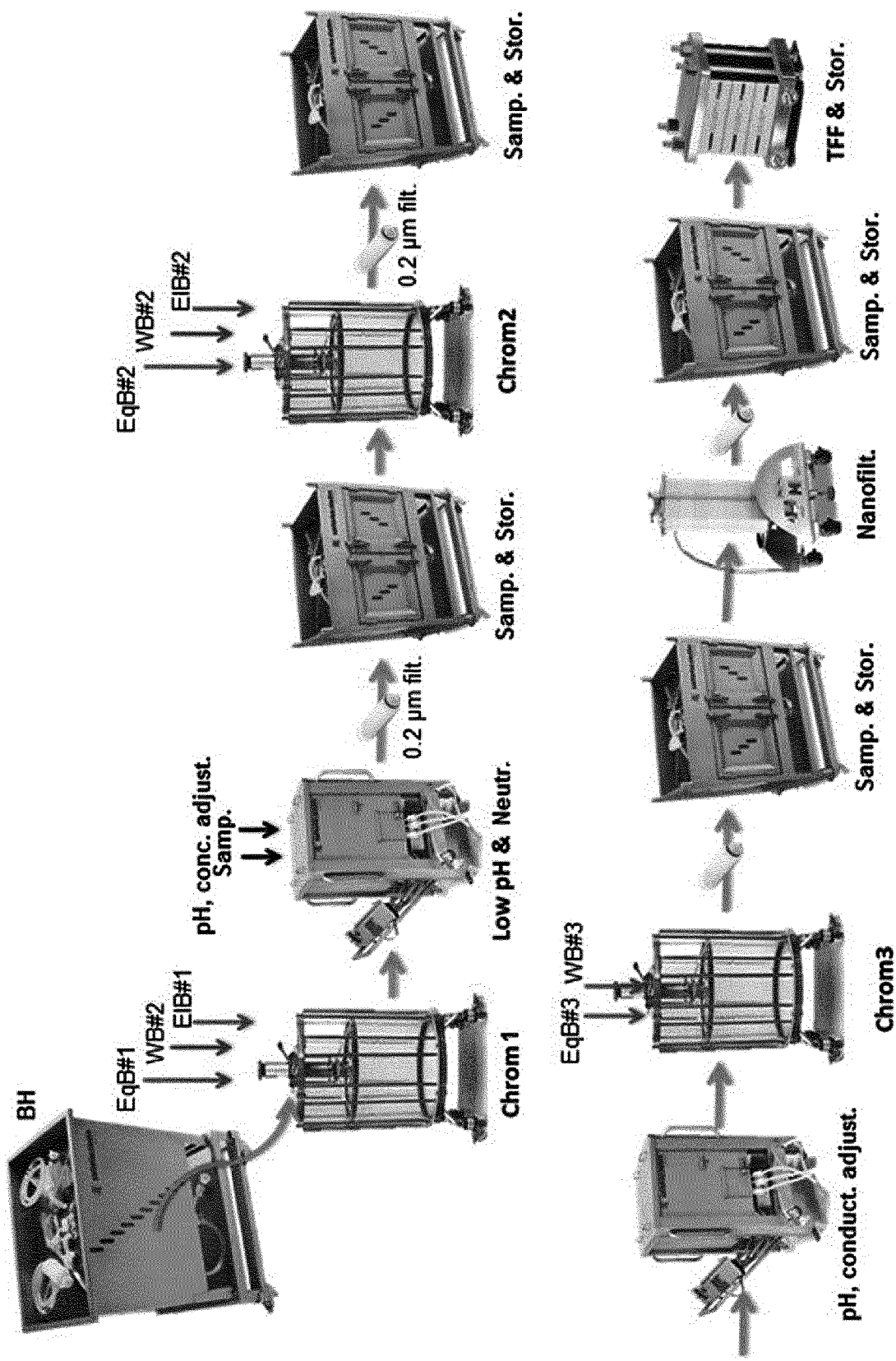
FIG. 5 shows a schematic of the different steps of a conventional process for purifying proteins. BH: bulk harvest; EqB #1: first equilibration buffer; WB #1: first wash buffer, EIB #1: first elution buffer; EqB #2: second equilibration buffer; WB #2: second wash buffer, EIB #2: second elution buffer; EqB #3: third equilibration buffer; WB #3: third wash buffer; chrom1: first chromatographic step; chrom2: second chromatographic step; chrom3: third chromatographic step; pH adjust.: pH adjustment; conc. adjust.: concentration adjustment; conduct. adjust.: conductivity adjustment; samp.: sampling; stor.: storage; filt.: filtration; Nanofilt.: nanofiltration; TFF: tangential flow filtration.
Figure 6:
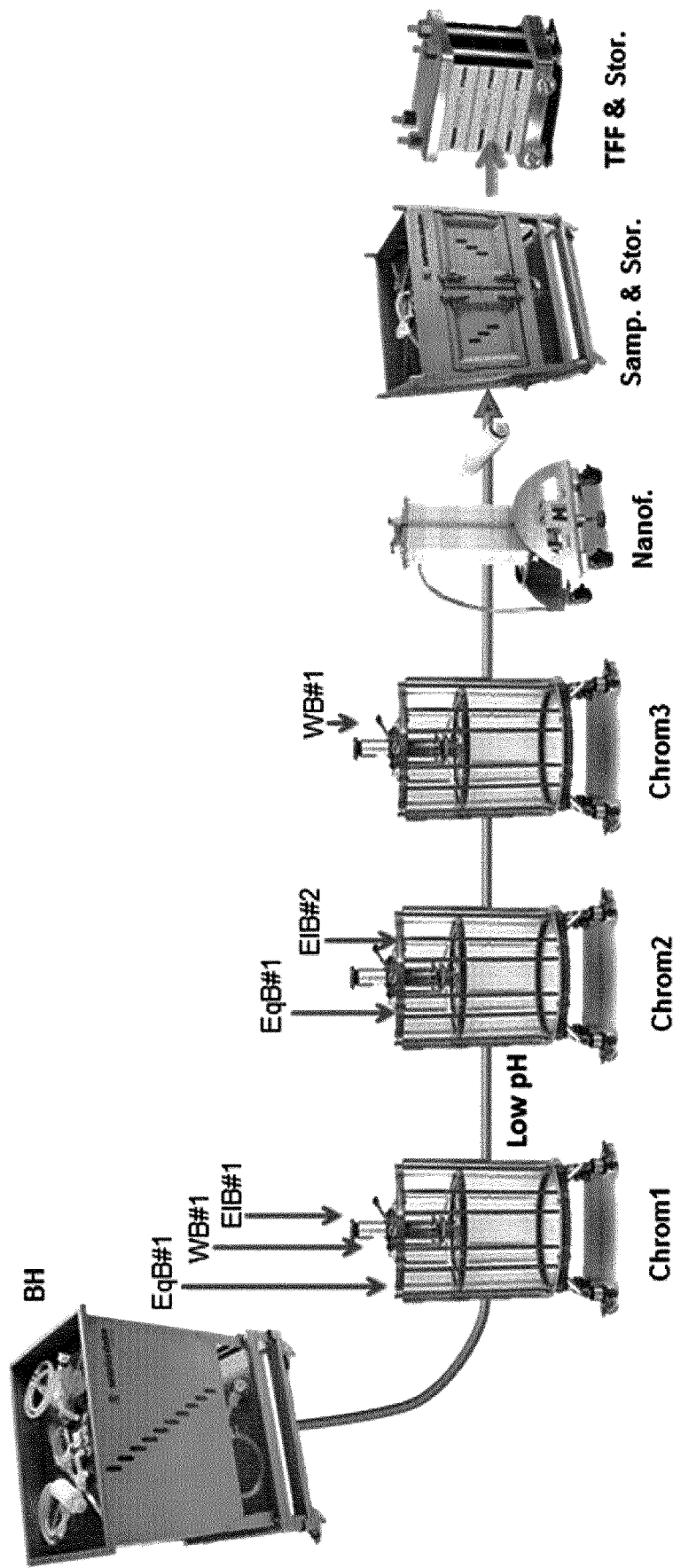
FIG. 6 shows a schematic of the different steps of the method of the invention. BH: bulk harvest; EqB #1: first equilibration buffer; WB #1: first wash buffer, EIB #1: first elution buffer; EIB #2: second elution buffer; chrom1: first chromatographic step; chrom2: second chromatographic step; chrom3: third chromatographic step; samp.: sampling; stor.: storage; Nanof.: nanofiltration; TFF: tangential flow filtration.
Figure 7:
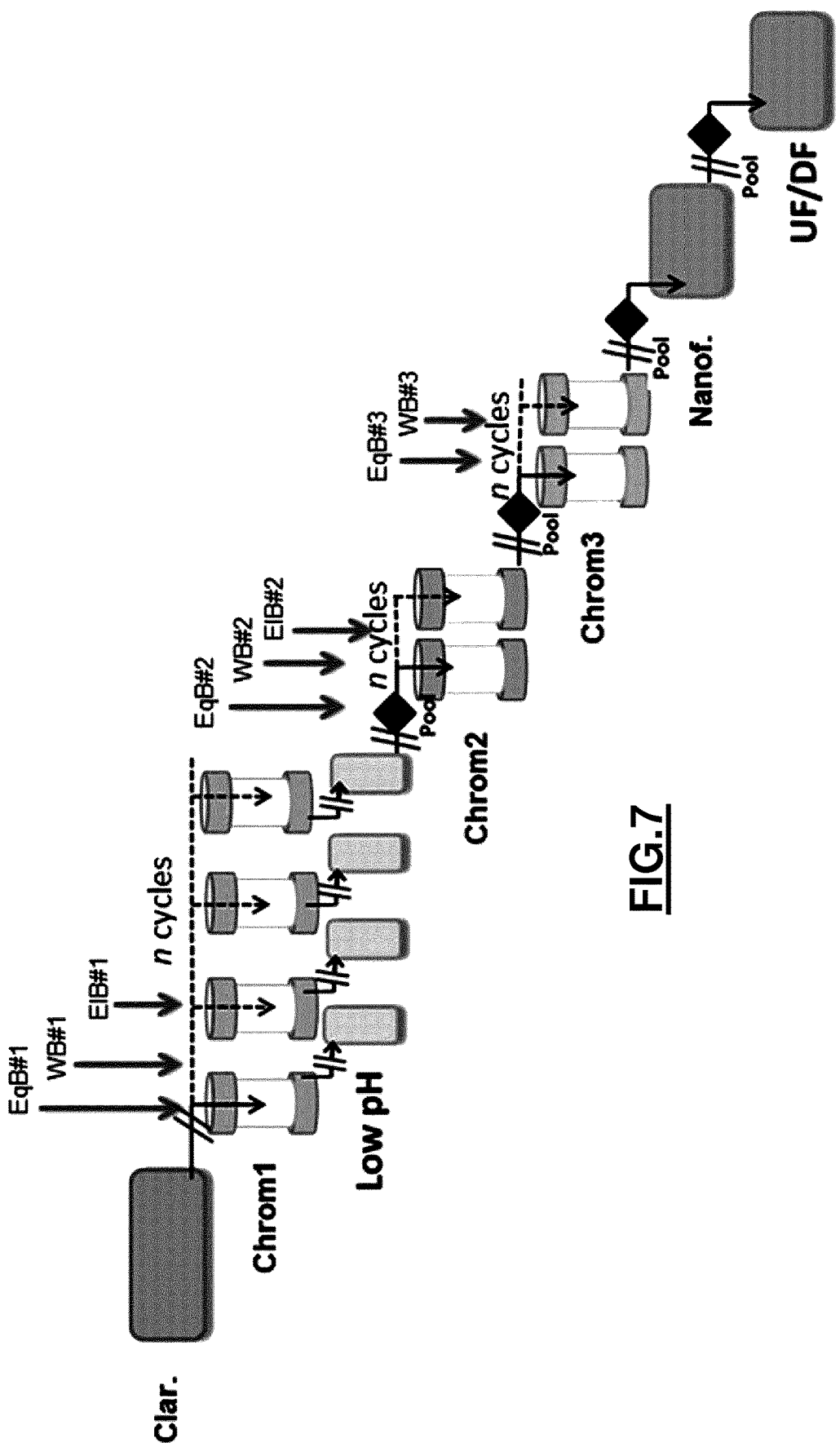
FIG. 7 shows a schematic of the different steps of a conventional process for purifying proteins including several runs or cycles. Clar.: clarification; EqB #1: first equilibration buffer; WB #1: first wash buffer, EIB #1: first elution buffer; EqB #2: second equilibration buffer; WB #2: second wash buffer, EIB #2: second elution buffer; EqB #3: third equilibration buffer; WB #3: third wash buffer; chrom1: first chromatographic step; chrom2: second chromatographic step; chrom3: third chromatographic step; Nanof.: nanofiltration; UF/DF: ultrafiltration/diafiltration.
Figure 8:
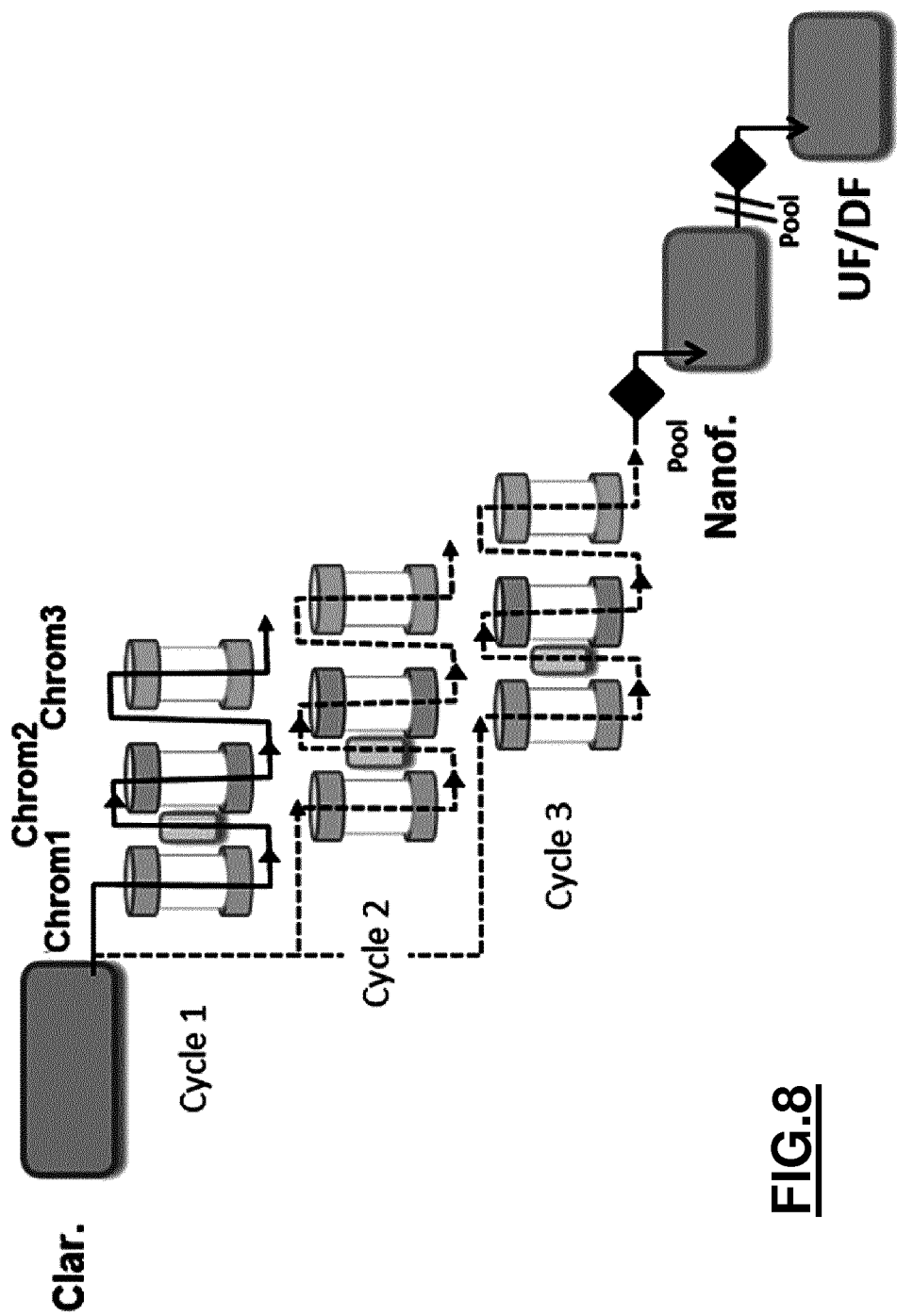
FIG. 8 shows a schematic of the different steps of the method of the invention including several runs or cycles. Clar.: clarification; EqB #1: first equilibration buffer; WB #1: first wash buffer, EIB #1: first elution buffer; EIB #2: second elution buffer; chrom1: first chromatographic step; chrom2: second chromatographic step; chrom3: third chromatographic step; Nanof.: nanofiltration; UF/DF: ultrafiltration/diafiltration.
Figure 9:
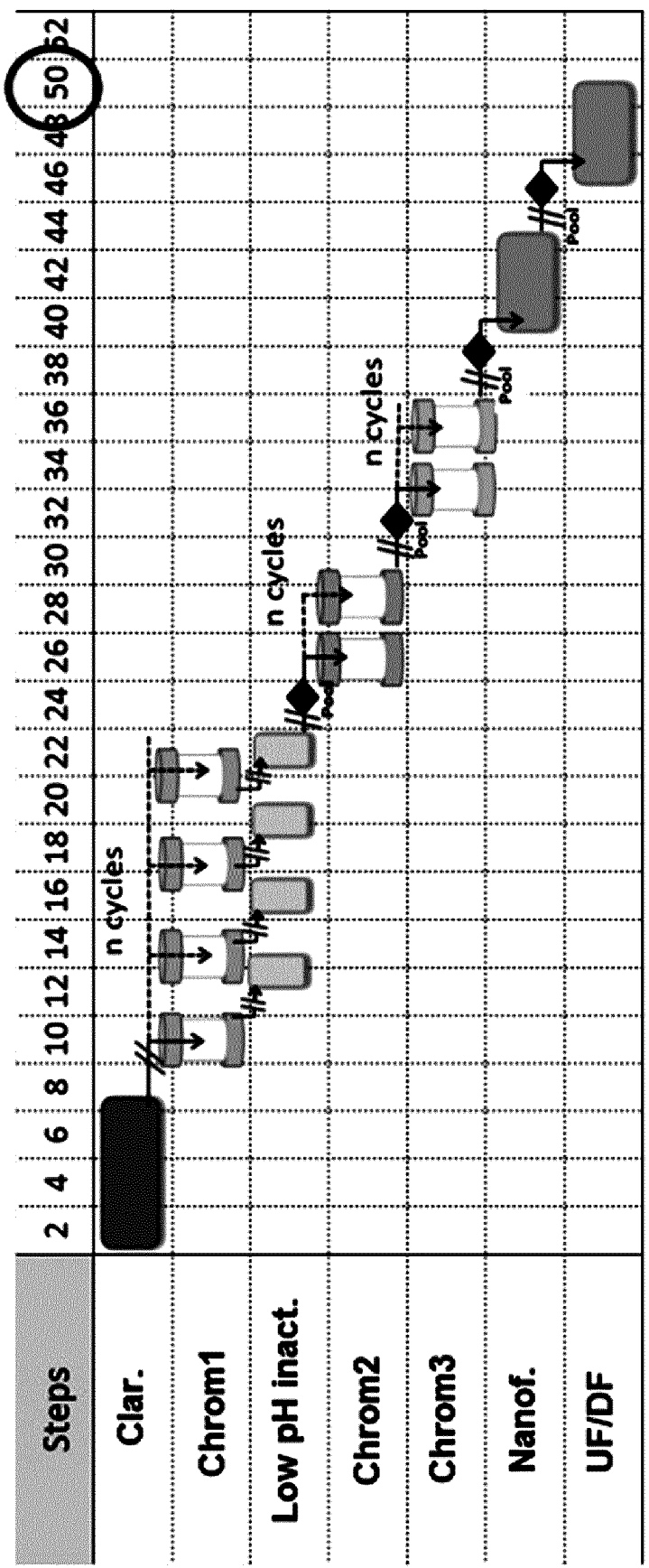
FIG. 9 shows a schematic of a timeline of the different steps of a conventional process for purifying proteins including several runs or cycles. The first line of the table shows time in hours. Clar.: clarification; chrom1: first chromatographic step; chrom2: second chromatographic step; chrom3: third chromatographic step; Low pH inact.: low pH inactivation; Nanof.: nanofiltration; UF/DF: ultrafiltration/diafiltration. The circle represents the time when the process is completed.
Figure 10:
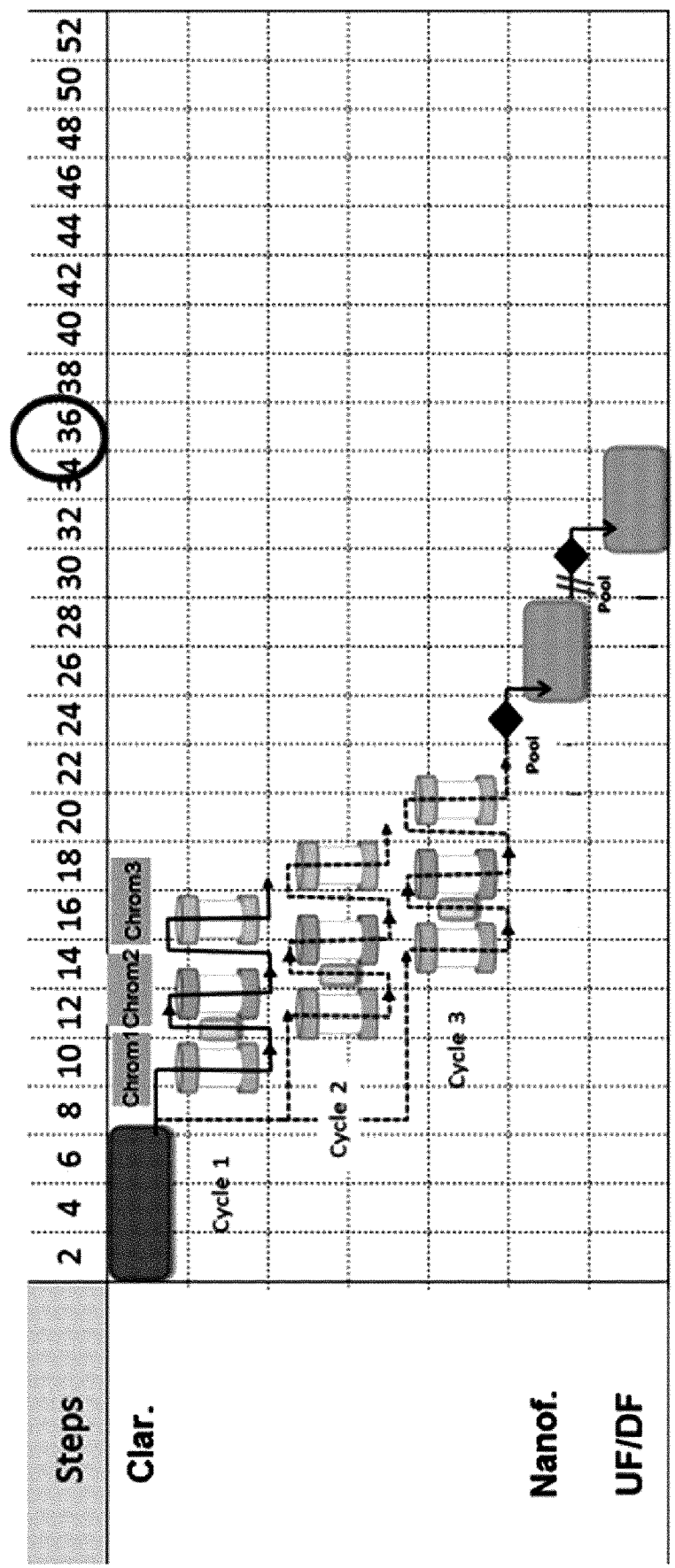
FIG. 10 shows a schematic of a timeline of the different steps of the method of the invention including several runs or cycles. Clar.: clarification; chrom1: first chromatographic step; chrom2: second chromatographic step; chrom3: third chromatographic step; Nanof.: nanofiltration; UF/DF: ultrafiltration/diafiltration. The circle represents the time when the process is completed.
Figure 11:
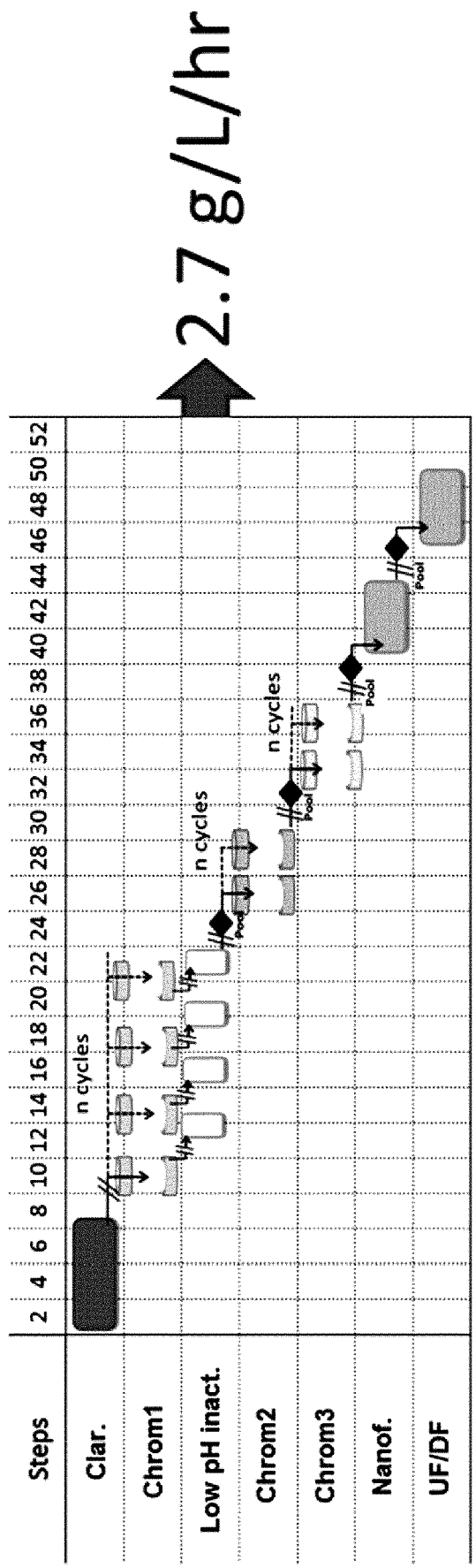
FIG. 11 shows a schematic of a timeline of the different steps of a conventional process for purifying proteins including several runs or cycles. The first line of the table shows time in hours. Clar.: clarification; chrom1: first chromatographic step; chrom2: second chromatographic step; chrom3: third chromatographic step; Low pH inact.: low pH inactivation; Nanof.: nanofiltration; UF/DF: ultrafiltration/diafiltration. The estimate level of productivity of the process is indicated.
Figure 12:
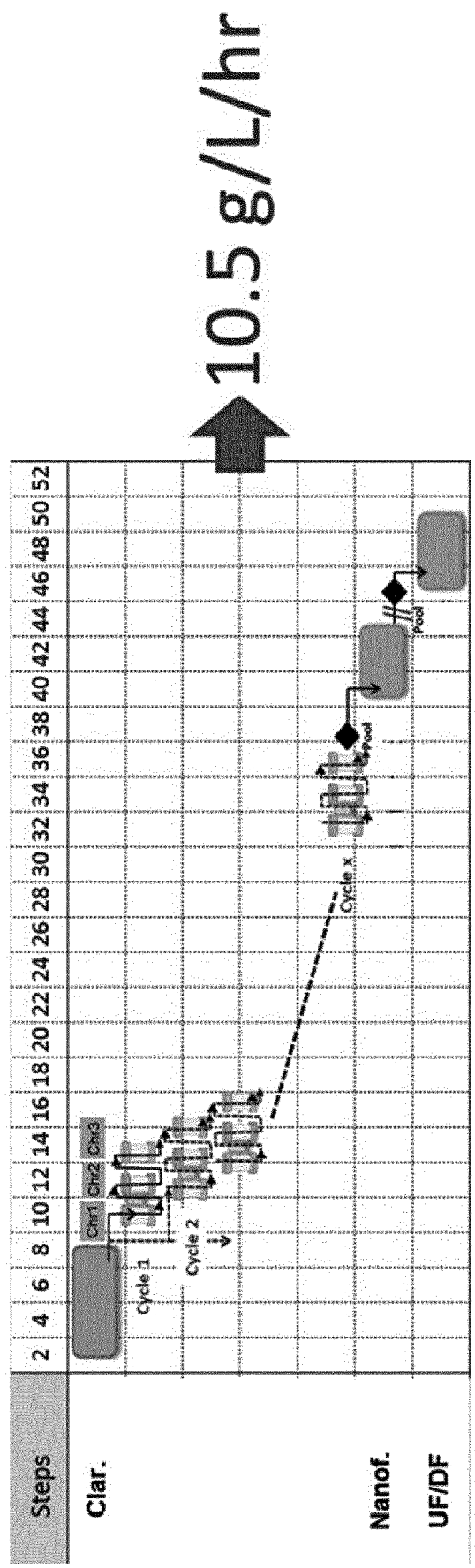
FIG. 12 shows a schematic of a timeline of the different steps of the method of the invention including several runs or cycles. Clar.: clarification; chr1: first chromatographic step; chr2: second chromatographic step; chr3: third chromatographic step; Nanof.: nanofiltration; UF/DF: ultrafiltration/diafiltration. The estimate level of productivity of the process is indicated.

Additionally, as shown in FIG. 4, trends did not show any significant differences between each run. Accordingly, the inventors surprisingly demonstrated that disposable membrane adsorbers were in fact stable and could be re-used over 50 runs without any performance decrease.

The main advantages of using membrane adsorbers rather than columns in the method of the invention are summarized below:

at comparable scale, membrane adsorbers can be used at a 10 fold higher flow rate than a column, thereby drastically reducing the duration of the process. For example, a 5 mL-column packed with resin will be used at a flow rate of 1 mL/min, whereas a corresponding 5 mL-membrane adsorber will be used at a minimum flow rate of 10 mL/min. Accordingly, when the 3 chromatographic steps process of the invention is performed in 2 h 30 using 3 columns packed with resins, it can be completed in 15 min using membrane adsorbers.

even if they are re-usable, membrane adsorbers are disposable devices, which can thus be discarded after a batch and do not need to be stored over a long term. It is therefore not necessary to test them to ensure long-term stability.

the method of the invention using membrane adsorbers is cheaper by avoiding column cost, column packing and column storage.

Example 9: GMP Scale Continuous MultiStep Process

The above method was applied to large-scale purification of a humanized monoclonal antibody that specifically binds to the CD38 transmembrane glycoprotein (anti-CD38 mAb).

Materials and Methods

Materials

First step: 6 L MabSelect Sure resin with a dynamic binding capacity (DBC) of 35 mg/mL Second step: 6 L Capto MMC resin with a DBC of 35 mg/mL Third step: 6 L BioPro Q75 resin with a DBC of 170 mg/mL 2 AktaProcess from GE (piloting the 3 columns) and one Flexact from Sartorius (completing a step of inactivating at low pH, between First step and Second step), comprising the above 3 columns on line and enabling monitoring of all columns.

Methods

A sequence of 7 runs was performed continuously.

Results

A sequence enabled purifying 1.3 Kg of anti-CD38 mAb in less than 16 h.

14.4 Kg of bulk harvest were loaded and 1.30 Kg of purified mAb were recovered. The Continuous Multistep Process of the invention thus enabled reaching an average yield of 90%. These 1.3 Kg of purified mAb were obtained in 16 h.

As a matter of comparison, the purification of a 500 L batch with a 2-step process takes 3 days and uses 20 L columns. The Continuous approach according to the invention is therefore an evolution allowing saving time and raw materials (saves more than 66% resins volume).

Additionally, the analytical results of the final product were comparable with the ones of the final product obtained with the 2-step process described in PCT/EP2012/059528. These analytical results are summarized in the table below.

|  | Bulk harvest | Current Process (2-steps process) and without low pH treatment | Continuous Multistep Process |
| --- | --- | --- | --- |
| Yield (%) |  | 95 | 90 |
| HMW (%) | 6.5 | 0.9 | 1.3 |
| HCP (ppm) | $3 \times 10^5$ | 5 | 5 |
| DNA (ppb) | $3 \times 10^6$ | <0.1 | <0.1 |

The invention claimed is:

1. A method for purifying a protein from solution comprising:
    (a) a first chromatography step comprising:
        passing said solution over a first chromatography matrix, wherein the first chromatography matrix is a Protein A affinity chromatography matrix;
        eluting a crude protein eluent from the first chromatography matrix using a first elution buffer;
    (b) a second chromatography step comprising:
        passing the crude protein eluent obtained at the end of step (a) over a second chromatography matrix;
        eluting a protein eluate from the second chromatography matrix using a second elution buffer; and
    (c) a third chromatography step comprising:
        passing the protein eluate obtained at the end of step (b) through a third chromatography matrix in the flow-through mode;
        recovering purified protein from the flow-through of the third chromatography matrix;
    wherein the protein is a monoclonal antibody, wherein each of the buffers comprises Bis Tris, acetic acid, NaCl, and water, wherein one or more of the buffers further comprises NH$_4$Cl, and wherein the method is a large-scale purification method.

2. The method of claim 1, wherein the crude protein eluent obtained at the end of step (a) is directly passed over a second chromatography matrix, without undergoing pH adjustment, buffer exchange or dilution.

3. The method of claim 1, wherein the protein eluate obtained at the end of step (b) is directly passed over a third chromatography matrix, without undergoing pH adjustment, buffer exchange or dilution.

4. The method of claim 1, wherein the method is run in a closed system from the first step to the last one.

5. The method of claim 1, wherein each one of the two first chromatography steps comprises successively:
    (i) passing an equilibration buffer over the chromatography matrix;
    (ii) passing the solution or the crude protein eluent over the chromatography matrix;
    (iii) passing the equilibration buffer over the chromatography matrix;
    (iv) optionally passing wash buffer over the chromatography matrix;
    (v) optionally passing the equilibration buffer over the chromatography matrix; and
    (vi) eluting the crude protein eluent or the protein eluate from the chromatography matrix using an elution buffer,
    wherein each of the buffers comprises Bis Tris.

6. The method of claim 5, wherein the equilibration buffer comprises 15 to 25 mM Bis Tris, and 15 to 25 mM NaCl, adjusted to a pH comprised between 7 and 8 with acetic acid.

7. The method of claim 5, wherein the wash buffer comprises of 15 to 25 mM Bis Tris, and 0.9 to 1.1 M NaCl adjusted to a pH comprised between 7 and 8 with acetic acid.

8. The method of claim 1, wherein said method comprises the steps of:
    (a) a first chromatography step comprising successively:
        (i) passing an equilibration buffer over a first chromatography matrix;
        (ii) passing the solution over the first chromatography matrix;
        (iii) passing the equilibration buffer over the first chromatography matrix;
        (iv) passing wash buffer over the first chromatography matrix;
        (v) passing the equilibration buffer over the first chromatography matrix; and
        (vi) eluting a crude protein eluent from the first chromatography matrix using a first elution buffer;
    (b) a second chromatography step comprising successively:
        (i) passing the equilibration buffer over a second chromatography matrix;

(ii) passing the crude protein eluent from step (a) over the second chromatography matrix;
(iii) passing the equilibration buffer over the second chromatography matrix; and
(iv) eluting a protein eluate from the second chromatography matrix using a second elution buffer;

and (c) a third chromatography step comprising successively:
passing the equilibration buffer over a third chromatography matrix;
(ii) passing the protein eluate from step (b) over the third chromatography matrix in the flow-through mode;
(iii) optionally passing wash buffer over the third chromatography matrix; and
(iv) recovering purified protein from the flow-through of the third chromatography matrix.

9. The method of claim 1, wherein the first, second and third chromatography matrices are chromatography columns.

10. The method of claim 1, wherein the first, second and third chromatography matrices are chromatography membrane adsorbers.

11. The method of claim 1, wherein the second chromatography matrix is a multi-modal resin chromatography matrix or a cation-exchange chromatography matrix.

12. The method of claim 1, wherein the third chromatography matrix is an anion-exchange chromatography matrix.

13. The method of claim 1, wherein said monoclonal antibody is selected from the group consisting of an antibody that specifically binds to the protofibrillar form of the human β-amyloid protein, an antibody that specifically binds to the bacterial surface polysaccharide poly-N-acetyl glucosamine (PNAG), an antibody that specifically binds to Carcinoembryonic antigen-related cell adhesion molecule 5 (CEACAM5) and an antibody that specifically binds to the CD38 transmembrane glycoprotein.

14. The method of claim 1, further comprising a nanofiltration step after step (c).

15. The method of claim 14, further comprising an ultrafiltration and diafiltration step after the nanofiltration step.

16. The method of claim 1, wherein the first elution buffer comprises 15 to 25 mM Bis Tris, and 15 to 25 mM NaCl, adjusted to a pH comprised between 3 and 4 with acetic acid.

17. The method of claim 1, wherein the second elution buffer comprises 15 to 25 mM Bis Tris, 40 to 50 mM NaCl, and 20 to 30 mM $NH_4Cl$, adjusted to a pH comprised between 7 and 8 with acetic acid.

18. The method of claim 1, wherein the second elution buffer comprises 15 to 25 mM Bis Tris, 50 to 150 mM NaCl, and 20 to 30 mM $NH_4Cl$, adjusted to a pH comprised between 6 and 7 with acetic acid.

19. The method of claim 1, wherein the purified protein is recovered with a yield of at least 95%.

20. The method of claim 1, wherein the recovered purified protein exhibits a purity of at least 99%.

21. The method of claim 1, further comprising the step of formulating the recovered purified protein into a pharmaceutical composition.

22. A method for purifying a protein from solution comprising:
(a) a first chromatography step comprising:
passing said solution over a first chromatography matrix, wherein the first chromatography matrix is a Protein A affinity chromatography column;
eluting a crude protein eluent from the first chromatography matrix using a first elution buffer;
(b) a second chromatography step comprising:
passing the crude protein eluent obtained at the end of step (a) over a second chromatography matrix, wherein the second chromatography matrix is a multi-modal resin chromatography column;
eluting a protein eluate from the second chromatography matrix using a second elution buffer; and
(c) a third chromatography step comprising:
passing the protein eluate obtained at the end of step (b) through a third chromatography matrix in the flow-through mode, wherein the third chromatography matrix is an anion-exchange chromatography column;
recovering purified protein from the flow-through of the third chromatography matrix;
wherein the protein is a monoclonal antibody, wherein each of the buffers comprises Bis Tris, acetic acid, NaCl, and water, and wherein the method is a large-scale purification method.

23. A method for purifying a protein from solution comprising:
(a) a first chromatography step comprising:
passing said solution over a first chromatography matrix, wherein the first chromatography matrix is a Protein A membrane adsorber;
eluting a crude protein eluent from the first chromatography matrix using a first elution buffer;
(b) a second chromatography step comprising:
passing the crude protein eluent obtained at the end of step (a) over a second chromatography matrix, wherein the second chromatography matrix is a cation-exchange membrane adsorber;
eluting a protein eluate from the second chromatography matrix using a second elution buffer; and
(c) a third chromatography step comprising:
passing the protein eluate obtained at the end of step (b) through a third chromatography matrix in the flow-through mode, wherein the third chromatography matrix is an anion-exchange membrane adsorber;
recovering purified protein from the flow-through of the third chromatography matrix;
wherein the protein is a monoclonal antibody, wherein each of the buffers comprises Bis Tris, acetic acid, NaCl, and water, and wherein the method is a large-scale purification method.

* * * * *